US012440654B2

(12) United States Patent
Nagata et al.

(10) Patent No.: US 12,440,654 B2
(45) Date of Patent: Oct. 14, 2025

(54) BALLOON-EQUIPPED TREATMENT TOOL FOR ENDOSCOPE, AND METHOD OF FOLDING BALLOON-EQUIPPED TREATMENT TOOL FOR ENDOSCOPE

(71) Applicant: OLYMPUS CORPORATION, Tokyo (JP)

(72) Inventors: Kazuhiro Nagata, Tokyo (JP); Kenji Ono, Musashino (JP); Norichika Fukushima, Hino (JP); Yasunori Oki, Hachioji (JP); Daijiro Kubota, Tokyo (JP)

(73) Assignee: OLYMPUS CORPORATION, Tokyo (JP)

( * ) Notice: Subject to any disclaimer, the term of this patent is extended or adjusted under 35 U.S.C. 154(b) by 566 days.

(21) Appl. No.: 17/680,886

(22) Filed: Feb. 25, 2022

(65) Prior Publication Data

US 2022/0175222 A1 Jun. 9, 2022

Related U.S. Application Data

(63) Continuation of application No. PCT/JP2019/036368, filed on Sep. 17, 2019.

(51) Int. Cl.
*A61M 25/10* (2013.01)

(52) U.S. Cl.
CPC .... *A61M 25/1029* (2013.01); *A61M 25/1002* (2013.01); *A61M 2025/1004* (2013.01)

(58) Field of Classification Search
CPC .......... A61M 25/1029; A61M 25/1002; A61M 2025/1004; A61M 25/104;
(Continued)

(56) References Cited

U.S. PATENT DOCUMENTS 5,733,301 A 3/1998 Forman
2006/0182873 A1* 8/2006 Klisch .................. A61M 25/10 427/2.1

(Continued)

FOREIGN PATENT DOCUMENTS

EP 0 414 350 A1 2/1991
JP 03-092173 A 4/1991

(Continued)

OTHER PUBLICATIONS

International Search Report dated Nov. 19, 2019 received in PCT/JP2019/036368.

*Primary Examiner* — Shaun L David
*Assistant Examiner* — Rachael L Geiger
(74) *Attorney, Agent, or Firm* — Scully, Scott, Murphy & Presser, P.C.

(57) ABSTRACT

According to one aspect, a balloon-equipped treatment tool for an endoscope includes a balloon, and a sheath connected to a proximal end side of the balloon and configured to introduce fluid to the balloon. The balloon includes a body portion having a first wall thickness, a cylindrical tail portion arranged on a proximal end side of the body portion and connected to the sheath, a cone portion located between the body portion and the tail portion, and a thick portion forming a second wall thickness larger than the first wall thickness. The thick portion whose distal end is arranged in the cone portion and whose proximal end is arranged in the tail portion.

17 Claims, 13 Drawing Sheets

(58) Field of Classification Search
CPC .. A61M 2025/1059; A61M 2025/1084; A61M 2025/1086; A61M 29/00; A61M 29/02; A61M 2029/025; A61B 1/00082
See application file for complete search history.

(56) References Cited

U.S. PATENT DOCUMENTS

| | | | | |
|---|---|---|---|---|
| 2006/0276820 | A1 | 12/2006 | Yamaguchi et al. | |
| 2015/0012032 | A1* | 1/2015 | Cox | A61M 25/1002 606/192 |
| 2015/0021834 | A1 | 1/2015 | Osumi et al. | |
| 2016/0144156 | A1* | 5/2016 | Zhou | B23K 26/0626 604/103.08 |
| 2019/0254849 | A1* | 8/2019 | Olson, Jr. | A61F 2/89 |

FOREIGN PATENT DOCUMENTS

| | | | |
|---|---|---|---|
| JP | 09-192227 | A | 7/1997 |
| JP | 2006-239156 | A | 9/2006 |
| JP | 2006-340914 | A | 12/2006 |
| WO | 2004/101057 | A1 | 11/2004 |
| WO | 2013/094541 | A1 | 6/2013 |

* cited by examiner

BALLOON-EQUIPPED TREATMENT TOOL FOR ENDOSCOPE, AND METHOD OF FOLDING BALLOON-EQUIPPED TREATMENT TOOL FOR ENDOSCOPE

CROSS-REFERENCE TO RELATED APPLICATIONS

This application is a continuation application based on PCT Patent Application No. PCT/JP2019/036368, filed on Sep. 17, 2019, the entire content of which is hereby incorporated by reference.

BACKGROUND

Technical Field

The present invention relates to a balloon-equipped treatment tool for an endoscope, and a method of folding a balloon-equipped treatment tool for an endoscope.

Background Art

A technique for dilating a narrowed portion of a lumen such as a patient's digestive tract or blood vessel using a balloon-equipped treatment tool for endoscopy is known. This procedure is performed, for example, as follows. The operator first inserts the insertion portion of the endoscope into the patient's body so that the distal end of the endoscope comes to a position where the narrowed portion can be observed. The operator inserts the balloon-equipped treatment tool with the balloon folded into the treatment tool channel of the endoscope, and protrudes the balloon of the balloon-equipped treatment tool from the distal end of the treatment tool channel Next, while observing the balloon with an objective lens at the distal end of the endoscope, the operator inserts the balloon into the narrowed portion so that the balloon is positioned in the narrowed portion. The operator introduces fluid to the inside of the balloon through a sheath having a lumen inside that communicates with the balloon. As a result, the folding of the balloon is canceled and the balloon is expanded. The expansion of the balloon expands the narrowed portion around the balloon.

After that, the balloon is contracted by discharging the fluid existing inside the balloon through the lumen. Then, the balloon is removed from the dilated narrowed portion by pulling out the endoscopic balloon-equipped treatment tool from the treatment tool channel.

Such a procedure is performed while confirming the position and degree of expansion of the balloon in the image captured through the objective lens at the distal end of the endoscope.

For example, Japanese Patent Application, First Publication No. 2006-239156 Patent Document 1 describes a balloon-equipped treatment tool used for such a procedure.

SUMMARY

According to one aspect, a balloon-equipped treatment tool for an endoscope includes a balloon, and a sheath connected to a proximal end side of the balloon and configured to introduce fluid to the balloon. The balloon includes a body portion having a first wall thickness, a cylindrical tail portion arranged on a proximal end side of the body portion and connected to the sheath, a cone portion located between the body portion and the tail portion, and a thick portion forming a second wall thickness larger than the first wall thickness. The thick portion whose distal end is arranged in the cone portion and whose proximal end is arranged in the tail portion.

According to the balloon-equipped treatment tool for endoscopy in the above aspect, it is possible to suppress the occurrence of bump-shaped ridges in the balloon.

DETAILED DESCRIPTION OF THE PREFERRED EMBODIMENTS

Figure 1:
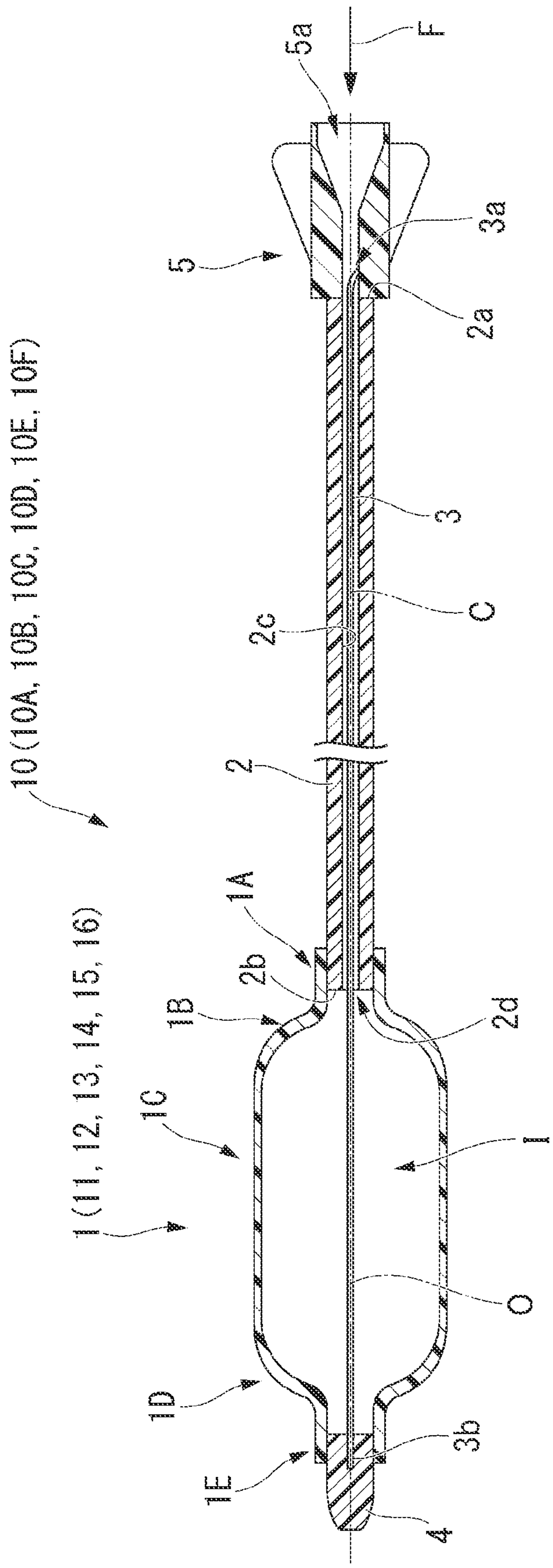
FIG. 1 is a schematic cross-sectional view showing an example of a balloon-equipped treatment tool for an endoscope according to a first embodiment of the present invention.

Hereinafter, embodiments of the present invention will be described with reference to the accompanying drawings. In all the drawings, even if the embodiments are different, the same or corresponding members are designated by the same reference numerals, and common description will be omitted.

First Embodiment

The balloon-equipped treatment tool for an endoscope according to a first embodiment of the present invention will be described.

Figure 2:
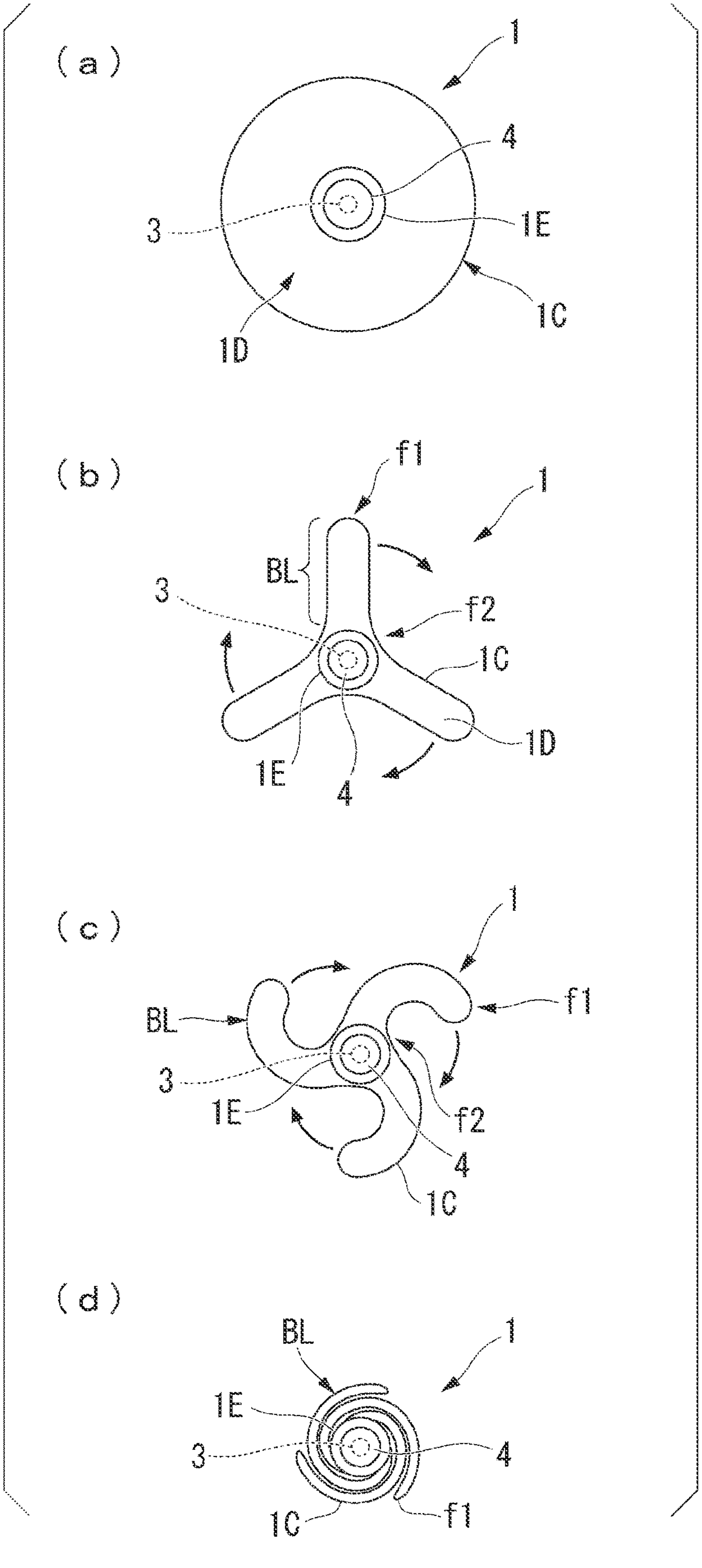
FIG. 2 is schematic side views showing how the balloon-equipped treatment tool according to the first embodiment of the present invention is folded.
Figure 3:
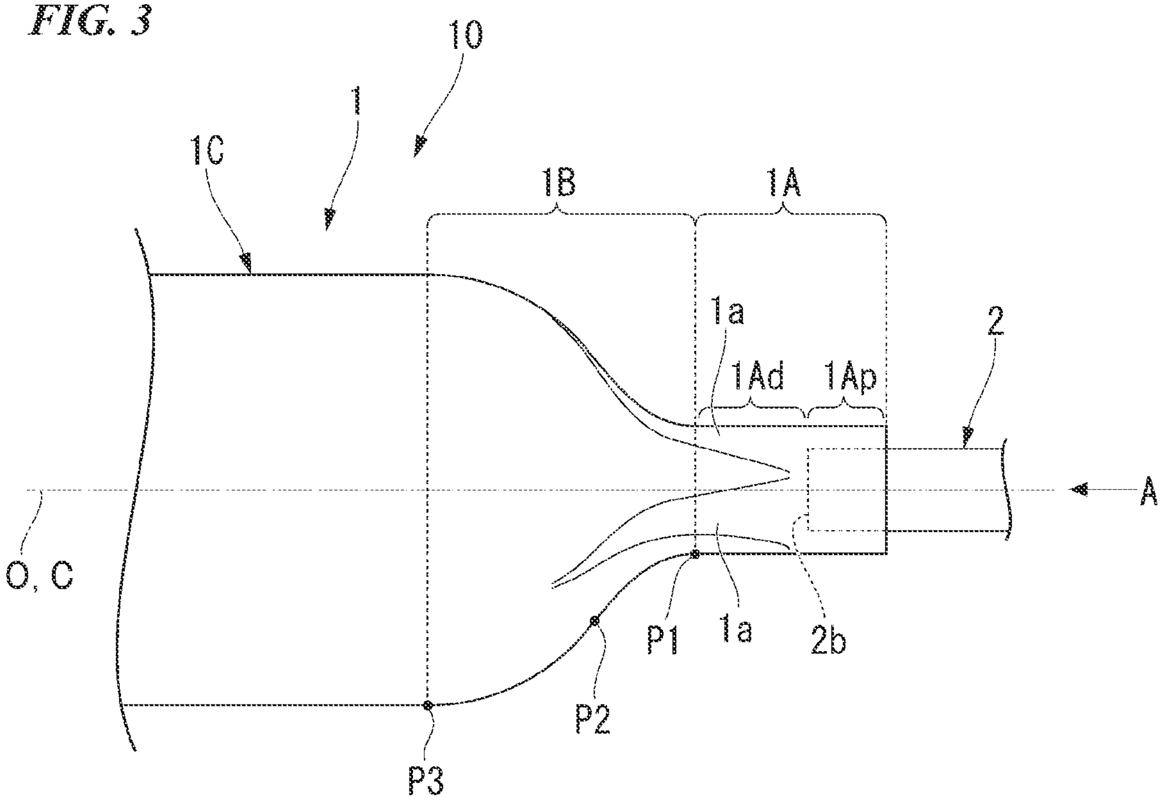
FIG. 3 is a schematic front view showing a proximal end portion of an example of the balloon-equipped treatment tool according to the first embodiment of the present invention.
Figure 4:
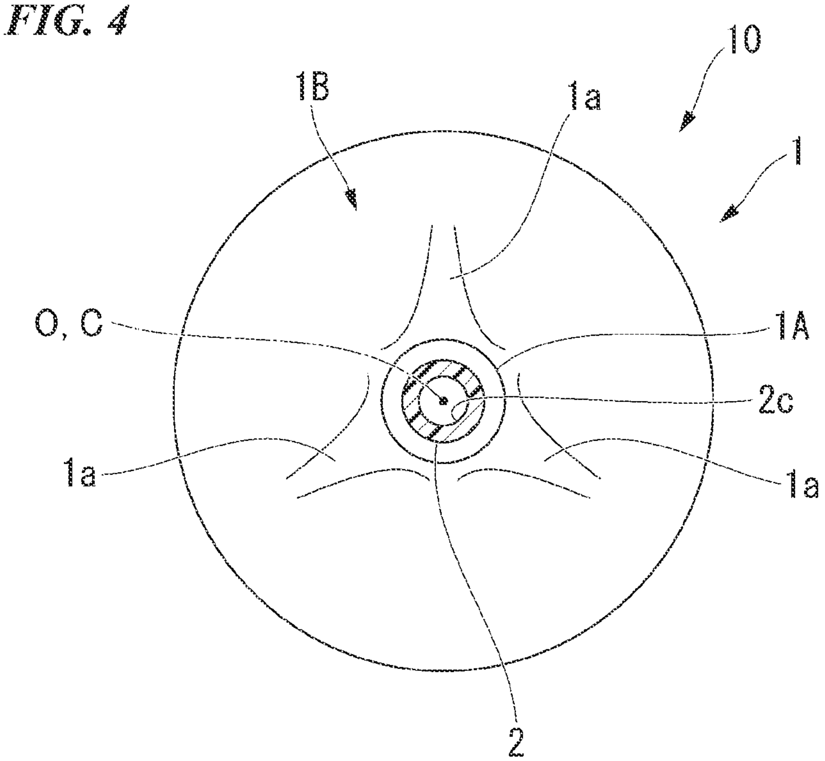
FIG. 4 is a view from an arrow A in FIG. 3.

FIG. 1 is a schematic cross-sectional view showing an example of a balloon-equipped treatment tool for an endoscope according to the first embodiment of the present invention. FIG. 2 is schematic side views showing how the balloon-equipped treatment tool according to the first embodiment of the present invention is folded. FIG. 3 is a schematic front view showing a proximal end portion of an example of a balloon-equipped treatment tool according to the first embodiment of the present invention. FIG. 4 is a view from an arrow A in FIG. 3.

As shown in FIG. 1, a balloon-equipped treatment tool 10 (balloon-equipped treatment tool for an endoscope) of the present embodiment is a long member extending from the proximal end on the right side of the drawing toward the distal end on the left side of the drawing. The balloon-equipped treatment tool 10 is inserted into the patient's lumen from the distal end through the treatment tool channel of an endoscope (not shown) inserted into the patient's lumen.

The balloon-equipped treatment tool 10 includes a sheath 2, a reinforcing wire 3, and a balloon 1. As will be described later, the balloon 1 can be expanded from the contracted state and contracted from the expanded state. FIG. 1 shows an expanded shape of the balloon 1.

In the following, in the balloon-equipped treatment tool 10 and the members constituting the balloon-equipped treatment tool 10, the direction along the axis is referred to as the axial direction, the direction around the axis is referred to as the circumferential direction, and the direction along the line intersecting the axis in the plane orthogonal to the axis is referred to as the radial direction. The axis can be defined with respect to an axial member or a cylindrical member, and corresponds to, for example, the central axis O of the balloon 1 and the central axis C of the sheath 2.

The balloon 1 before being inserted into the treatment tool channel of the endoscope is folded into a plurality of thin blades in the contracted state. (a) in FIG. 2 is a view of the balloon 1 in the expanded state, and (b) in FIG. 2 is a view of the balloon 1 in the contracted state as viewed from the distal end side. A fluid is discharged from the inside of the balloon 1 in the expanded state shown in (a) in FIG. 2 to make the balloon 1 transition to the contracted state. At this time, by pressing the balloon 1 from the periphery of the balloon 1 with a mold or the like (not shown), a plurality of blades BL are formed at different positions in the circumferential direction in the balloon 1 ((b) in FIG. 2). In (b) in FIG. 2, three blades BL are formed, but the number of blades BL is not limited to three.

Each blade BL is formed by alternately applying mountain folds and valley folds to the balloon 1 in a direction parallel to the axis.

A mountain fold is formed by a folding method in which the inner surfaces of the balloon 1 are bent so as to face each other. At the distal end of each blade BL, a mountain fold portion f1 made of a crease made by a mountain fold is formed.

A valley fold is formed by a folding method in which the outer surfaces of the balloon 1 are bent so as to face each other. A valley fold portion f2 formed by a crease formed by a valley fold is formed between the blades BL adjacent to each other in the circumferential direction.

(c) in FIG. 2 shows how each of the formed blades BL is further wound around the reinforcing wire 3 extending along the central axis of the balloon 1. (d) in FIG. 2 shows a state in which the winding of the blade BL is completed.

As shown in (d) in FIG. 2, in the contracted state, the balloon 1 is folded into a plurality of blades and wound around the central axis of the balloon 1. As a result, the outer diameter of the balloon-equipped treatment tool 10 can be made as small as possible, and the balloon 1 is devised so that the channel for the treatment tool of the endoscope can be smoothly inserted.

The type of lumen into which the balloon-equipped treatment tool 10 is inserted is not limited. For example, the balloon-equipped treatment tool 10 may be inserted into the gastrointestinal tract such as the esophagus, pylorus, bile duct, and large intestine. The outer diameter of the balloon-equipped treatment tool 10 when the balloon 1 is contracted and the maximum outer diameter when the balloon 1 is expanded are preset according to the inner diameter of the lumen to be inserted and the channel for the treatment tool.

The sheath 2 is a long member that introduces the fluid F that expands the balloon 1 to the balloon 1. The fluid F may be a liquid or a gas.

The sheath 2 may be formed by a single tube or may be formed by a plurality of tubes. The sheath 2 may be a single-layer tube or a multi-layer tube.

Examples of the material of the sheath 2 include nylon, polyamide, PTFE (polytetrafluoroethylene), PE (polyethylene), PP (polypropylene) and the like.

Inside the sheath 2, a lumen 2*c* that penetrates from the proximal end 2*a* to the distal end 2*b* of the sheath 2 is formed. A reinforcing wire 3 is inserted in the lumen 2*c*.

The inner diameter of the lumen 2*c* is larger than the outer diameter of the reinforcing wire 3 described later. Therefore, the fluid F can flow through the lumen 2*c* with the reinforcing wire 3 inserted therein.

A base 5 connected to a fluid-introducing device (not shown) is connected to the proximal end 2*a* of the sheath 2. The lumen 2*c* at the proximal end 2*a* communicates with the opening 5*a* of the base 5.

The distal end 2*b* is formed with a distal end opening 2*d* that communicates with the lumen 2*c*.

The reinforcing wire 3 supports the balloon 1, which will be described later, substantially coaxially with the sheath 2. The reinforcing wire 3 has flexibility such that it can be bent depending on the magnitude of the external force acting through the lumen into which the balloon-equipped treatment tool 10 is inserted or the treatment tool channel Therefore, the reinforcing wire 3 can be curved along the lumen or the treatment tool channel.

The length of the reinforcing wire 3 is substantially equal to the sum of the lengths of the sheath 2 and the balloon 1.

The proximal end 3*a* of the reinforcing wire 3 is fixed to the base 5. The reinforcing wire 3 protrudes from the distal end opening 2*d* of the sheath 2 and extends in front of the distal end 2*b*. The distal end 3*b* of the reinforcing wire 3 is fixed to the distal end convex portion 4.

For example, as the material of the reinforcing wire 3, nickel-titanium alloy, stainless steel, or the like is used.

The distal end convex portion 4 is a rod-shaped member having an outer diameter substantially equal to the outer diameter of the sheath 2 except for the distal end portion. The distal end portion of the distal end convex portion 4 has a tapered shape and is rounded so that the diameter gradually decreases toward the distal end side.

The balloon 1 is softer than the sheath 2 and is made of a stretchable resin film. The shape of the balloon 1 is a cylinder centered on the central axis O in the expanded state.

Inside the balloon 1, the proximal end portion of the distal end convex portion 4, the reinforcing wire 3, and the distal end portion of the sheath 2 are inserted.

As will be described later, the proximal end portion of the balloon 1 is firmly fixed to the distal end portion of the sheath 2, and the distal end portion of the balloon 1 is closely fixed to the proximal end portion of the distal end convex portion 4. As a result, an internal space I communicating with the lumen 2*c* of the sheath 2 is formed inside the balloon 1. The fluid F introduced to the internal space I is held inside the balloon 1.

As shown in FIG. 1, the balloon 1 has a first tail portion 1A (tail portion), a first cone portion 1B (cone portion), a body portion 1C, a second cone portion 1D, and a second tail portion 1E from the proximal end side to the distal end side.

When the reinforcing wire 3 extends straight, the balloon 1 is arranged coaxially with the central axis C of the sheath 2.

As shown in FIG. 3, the first tail portion 1A of the balloon 1 is a cylindrical portion, and has a distal end portion 1Ad on the distal end side and a proximal end portion 1Ap on the proximal end side. The inner peripheral surface of the proximal end portion 1Ap is fixed in close contact with the outer peripheral surface of the distal end portion of the sheath 2. The wall thickness of the first tail portion 1A is constant except for variations due to manufacturing errors.

The method of fixing the first tail portion 1A to the sheath 2 is not particularly limited as long as the fluid F can be sealed inside. For example, the first tail portion 1A may be fixed to the outer peripheral surface of the sheath 2 by heat fusion or the like. Since the proximal end portion 1Ap is integrated with the sheath 2, it is equivalent to the sheath 2 in terms of flexibility and expandability. For example, the inner diameter and outer diameter of the proximal end portion 1Ap do not change even if the pressure of the fluid F changes.

On the other hand, in the first tail portion 1A, the distal end portion 1Ad closer to the distal end than the proximal end portion 1Ap is not fixed to the sheath 2.

Therefore, the distal end portion 1Ad has flexibility and expandability according to its rigidity.

The first cone portion 1B is a hollow portion whose diameter gradually increases from the distal end of the first tail portion 1A toward the body portion 1C described later. The first cone portion 1B is arranged coaxially with the central axis C of the sheath 2 when the reinforcing wire 3 (not shown) extends straight.

The rate of change in the diameter of the first cone portion 1B may be constant or may be changed. For example, the shape of the first cone portion 1B may be a conical surface, or may be various shapes curved outward or inward from the conical surface by changing the rate of change in diameter. For example, the shape of the first cone portion 1B may be a bowl type, a cannonball type, a bell type, a funnel type, a horn type, or the like.

For example, in the example shown in FIG. 3, the expansion ratio of the outer diameter of the first cone portion 1B gradually increases from the point P1 at the boundary with the first tail portion 1A, becomes maximum at the point P2, and gradually decreases from the point P2 toward the point P3 at the boundary with the body portion 1C. Taking a cross section including the point P2 and the central axis C, the point P2 is an inflection point of the inclination curve of the first cone portion 1B.

The wall thickness of the first cone portion 1B may change depending on the position in the axial direction, but if the positions in the axial direction are the same, the wall thickness in the circumferential direction is constant except for variations due to manufacturing errors.

The body portion 1C has a constant outer diameter from the distal end of the first cone portion 1B, and is a cylindrical portion centered on the central axis O. The body portion 1C is preferably smoothly connected to the distal end of the first cone portion 1B.

The wall thickness of the body portion 1C is substantially equal to the wall thickness of the distal end of the first cone portion 1B.

The length of the body portion 1C is set to an appropriate length according to the length of the narrowed portion.

The second cone portion 1D is a hollow portion whose diameter is gradually reduced from the distal end of the body portion 1C toward the second tail portion 1E described later. The second cone portion 1D may have the same configuration as the first cone portion 1B except that the thick portion 1*a* is not formed.

The second tail portion 1E is a cylindrical portion centered on the central axis O extending from the distal end of the second cone portion 1D. The proximal end portion of the second tail portion 1E is closely fixed to the outer peripheral surface of the distal end convex portion 4. The second tail portion 1E may have the same configuration as the first tail portion 1A except that the thick portion 1*a* is not formed.

The method of fixing the second tail portion 1E to the distal end convex portion 4 may be the same as the method of fixing the first tail portion 1A to the sheath 2.

Such a balloon 1 is formed of a resin material that can elastically expand and contract by the pressure of the fluid F. The material of the balloon 1 is preferably sufficiently translucent. It is more preferable that the transmittance of the material of the balloon 1 be close to 100%.

As the material of the balloon 1, it is more preferable that the shore hardness be large for the purpose of enabling expansion at a high-pressure resistance. For example, it is more preferable that a material having a shore hardness of D40 or higher be used for the shore hardness of the material of the balloon 1.

The balloon 1 may be formed of, for example, one or more resin materials selected from the group consisting of a polyamide elastomer and a polyamide resin.

When the balloon 1 is formed of a plurality of materials, different materials may be used depending on the site of the balloon 1. One part selected from the first tail portion 1A, the first cone portion 1B, the body portion 1C, the second cone portion 1D, the second tail portion 1E, and the thick portion 1*a* may be made of a material different from any other part.

When the balloon 1 is formed of a plurality of materials, for example, the plurality of materials may be laminated in the radial direction.

In the first tail portion 1A and the first cone portion 1B, a ridge-shaped thick portion 1*a* extending on the first tail portion 1A and the first cone portion 1B is formed. The thick portion 1*a* is a portion where the resin forming the balloon 1 rises like a mountain range, and is formed from the first tail portion 1A to the first cone portion 1B. The wall thickness of the first tail portion 1A or the first cone portion 1B in which the thick portion 1*a* is formed is thicker than the wall thickness of the first tail portion 1A or the first cone portion 1B in which the thick portion 1*a* is not formed by the amount of the ridge of the thick portion 1*a*.

The number of thick portions 1*a* is not particularly limited as long as the occurrence of bump-shaped ridges, which will be described later, can be suppressed. Considering that the balloon 1 is bent in various directions at the proximal end portion 1Ap, the number of the thick portions 1*a* is preferably a plurality, more preferably three or more. In the example shown in FIGS. 3 and 4, the number of thick portions 1*a* is 3. As shown in FIG. 3, each thick portion 1*a* extends from the distal end portion 1Ad to the first cone portion 1B in a ridge pattern.

It is preferable that the position of the distal end of the thick portion 1*a* be within the first cone portion 1B (unless it has advanced to the body portion 1C), because the state in which the blade BL of the balloon 1 is wound is realized with a small diameter as shown in (d) in FIG. 2. For example, the thick portion 1*a* may extend to the center of or near the center of the first cone portion 1B in the axial direction. For example, when the inclination curve of the first cone portion 1B has an inflection point, the thick portion 1*a* may extend to the inflection point or its vicinity. Here, the "neighborhood" is defined as a range of ±δ of the position of the center or the inflection point in the axial direction, where δ is 20% of the length of the first cone portion 1B in the axial direction.

It is preferable that the thick portion 1*a* extend to or near the inflection point, because the thick portion 1*a* hardly hinders the observation of the narrowed portion through the balloon 1 and a sufficient reinforcing effect can be obtained to suppress the occurrence of bump-shaped ridges.

In order to give uniform directionality to the bending at the proximal end portion 1Ap of the balloon 1, when there are a plurality of thick portions 1*a*, it is more preferable that the distance from the center of the first cone portion 1B to the distal end of each thick portion 1*a* be equal to or substantially equal to each other. Here, substantially equal is defined as the difference in the length of each thick portion 1*a* with respect to the average length of each thick portion 1*a* within the range of ±20% of the average length.

The detailed shape of the ridges in each thick portion 1*a* is not particularly limited. For example, the width of each thick portion 1*a* may be constant or may vary. Here, the width of the thick portion 1*a* is defined as a dimension perpendicular to the extending direction of the thick portion 1*a* and along the surface of the balloon 1. The wall thickness of the thick portion 1*a* is defined as a dimension perpendicular to the extending direction of the thick portion 1*a* and in the wall thickness direction of the balloon 1. When the width changes, it is more preferable to reduce the width monotonously in a broad sense from the proximal end to the distal end of the thick portion 1*a*. Here, narrowing to a monospaced font in a broad sense means that a monospaced change may be included in a part thereof.

In the example shown in FIG. 4, each thick portion 1*a* is narrowed monotonously in a narrow sense from the proximal end to the distal end. Here, narrowing monospaced in a narrow sense means not including a monospaced change.

In the thick portion 1*a*, it is more preferable that the width in the first tail portion 1A be wider than the width in the first cone portion 1B, but variations in the width change are possible.

Figure 5:
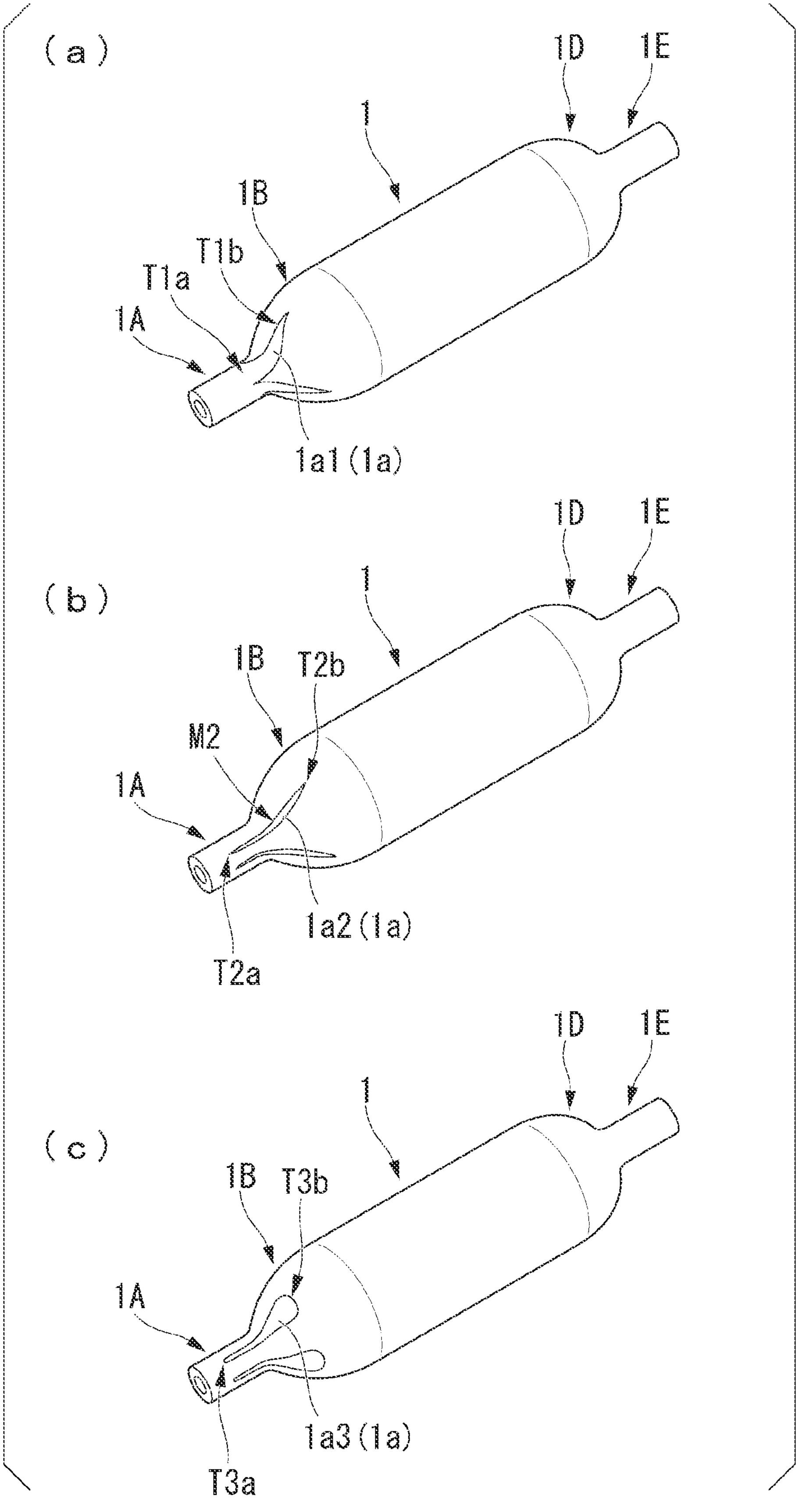
FIG. 5 is a schematic perspective view showing a variation example of a change in the width of a thick portion of the balloon-equipped treatment tool according to the first embodiment of the present invention.

FIG. 5 shows the thick portions 1*a*1, 1*a*2, and 1*a*3 as examples of variations in the width of the thick portion 1*a*.

In the example of the thick portion 1*a*1 shown in FIG. 5A, the width of the ridge-shaped thick portion 1*a*1 is narrowed from the proximal end T1*a* toward the distal end T1*b*. In the case of such a shape, since the area occupied by the thick portion 1*a*1 in the first cone portion 1B of the balloon 1 is smaller than the area occupied by the first tail portion 1A, it is narrowed through the first cone portion 1B of the balloon 1. When observing the portion with an endoscope, the degree to which the thick portion 1*a*1 interferes with the observation is low. Further, the presence of the thick portion 1*a*1 at the time of contraction of the balloon 1 hinders the formation of the blades to a low degree.

In the example of the thick portion 1*a*2 shown in FIG. 5B, the width of the ridge-shaped thick portion 1*a*2 is narrow at the proximal end T2*a* and the distal end T2*b*, and slightly wide at the intermediate portion M2. According to this shape, since the shape of the thick portion 1*a*2 becomes slender as a whole, there is an advantage in that the diameter of the blade BL after winding can be reduced as shown in (d) in FIG. 2.

In the example of the thick portion 1*a*3 shown in (c) in FIG. 5, the width of the ridge-shaped thick portion 1*a*3 widens from the proximal end T3*a* toward the distal end T3*b*. In the case of such a shape, the first cone portion 1B is less deformed when the proximal end portion of the balloon 1 is bent due to an angle operation. As a result, the occurrence of wrinkles and bump-shaped ridges is more effectively suppressed.

However, the variation of the change in the width of the thick portion 1*a* is not limited to the above example.

The extending direction of the thick portion 1*a* is not particularly limited as long as it is in the direction from the distal end portion 1Ad to the first cone portion 1B.

It is more preferable that the direction of the ridges of the thick portion 1*a* (extending direction) be along the longitudinal direction of the balloon 1 (direction along the central axis O). That is, it is more preferable that the thick portion 1*a* extend in the longitudinal direction of the balloon 1 when viewed from an appropriate radial direction. In other words, the center line extending in the extending direction of the thick portion 1*a* is included in an appropriate plane including the central axis O, and the thick portion 1*a* extends from the proximal end side of the balloon 1 toward the distal end side along the surfaces of the first tail portion 1A and the first cone portion 1B.

For example, in the example shown in FIG. 4, each thick portion 1*a* extends radially from the center of the first cone portion 1B when viewed from the axial direction. Further, each thick portion 1*a* extends in the radial direction so as to divide the circumference concentric with the first cone portion 1B into three equal parts. It is preferable that the direction in which each thick portion 1*a* viewed from the axial direction extends be radial, which divides the circumference into three or more equal parts, because it can evenly respond to bending of the distal end of the endoscope in various directions due to the angle operation.

When the thick portion 1*a* extends radially from the center of the first cone portion 1B, each thick portion 1*a* extends in the longitudinal direction of the balloon 1 (direction along the central axis O) when viewed from an appropriate radial direction.

It is preferable that each thick portion 1*a* extend radially from the center of the first cone portion 1B when viewed from the axial direction, as it is effective in suppressing the generation of bumps. However, when viewed from the axial direction, the stretching direction of the thick portion 1*a* may be inclined with respect to the radial direction. Further, the thick portion 1*a* may extend in a curved ridge shape.

In the example shown in FIG. 3, when viewed from an appropriate radial direction, each thick portion 1*a* extends in the longitudinal direction of the balloon 1, so the size of the width of the thick portion 1*a* can be measured in a cross section orthogonal to the central axis O (hereinafter, referred to as a cross section perpendicular to the axis). The width of the thick portion 1*a* may be constant or variable in the extending direction.

Figure 6A:
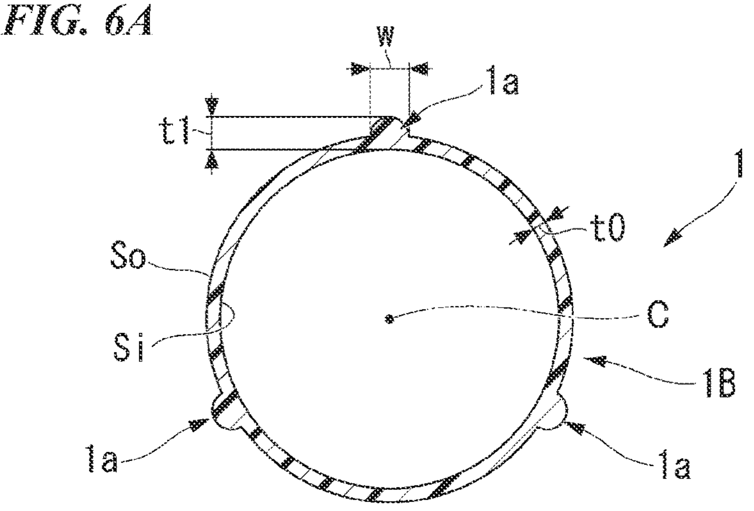
FIG. 6A is a schematic cross-sectional view showing an example of a cross section orthogonal to the central axis of the balloon in the balloon-equipped treatment tool according to the first embodiment of the present invention.
Figure 6B:
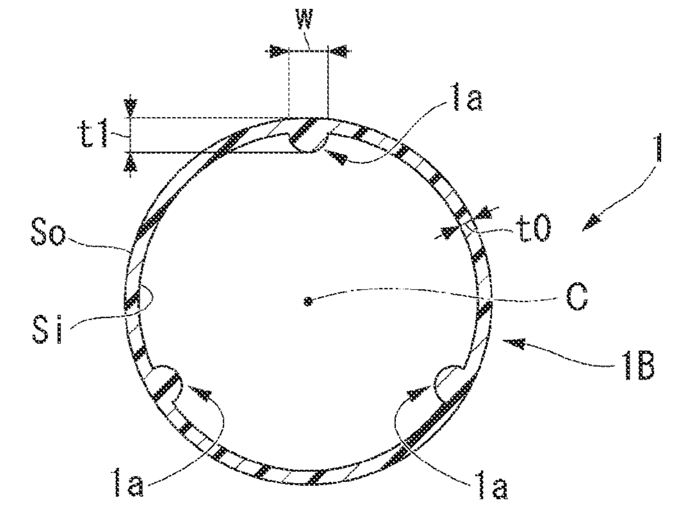
FIG. 6B is a schematic cross-sectional view showing an example of a cross section orthogonal to the central axis of the balloon in the balloon-equipped treatment tool according to the first embodiment of the present invention.
Figure 6C:
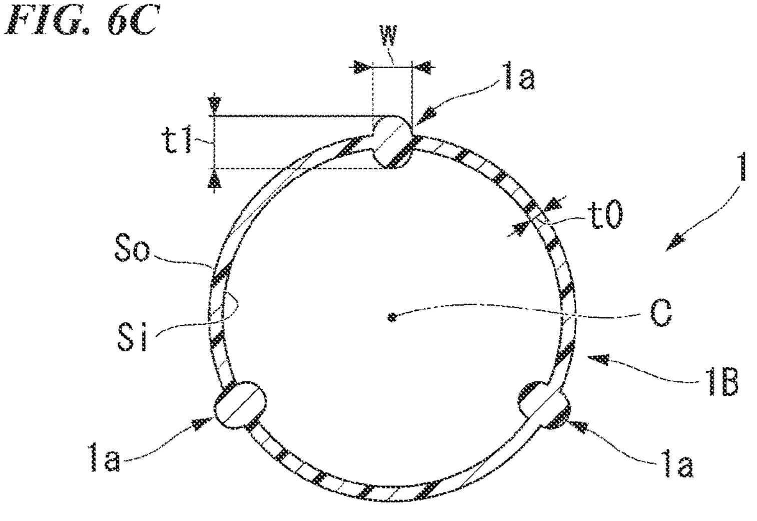
FIG. 6C is a schematic cross-sectional view showing an example of a cross section orthogonal to the central axis of the balloon in the balloon-equipped treatment tool according to the first embodiment of the present invention.
Figure 6D:
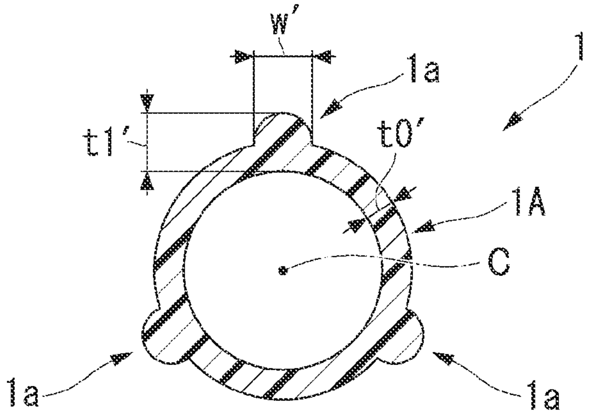
FIG. 6D is a schematic cross-sectional view showing an example of a cross section orthogonal to the central axis of the balloon in the balloon-equipped treatment tool according to the first embodiment of the present invention.
Figure 6E:
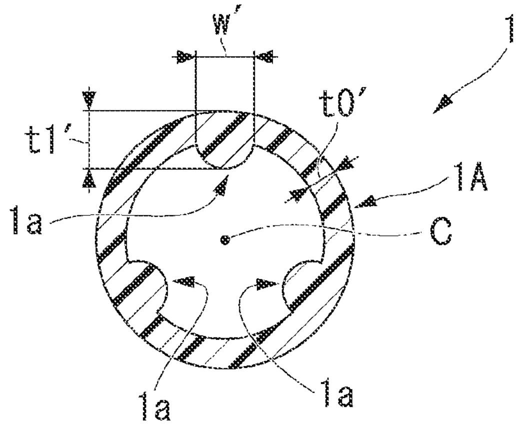
FIG. 6E is a schematic cross-sectional view showing an example of a cross section orthogonal to the central axis of the balloon in the balloon-equipped treatment tool according to the first embodiment of the present invention.
Figure 6F:
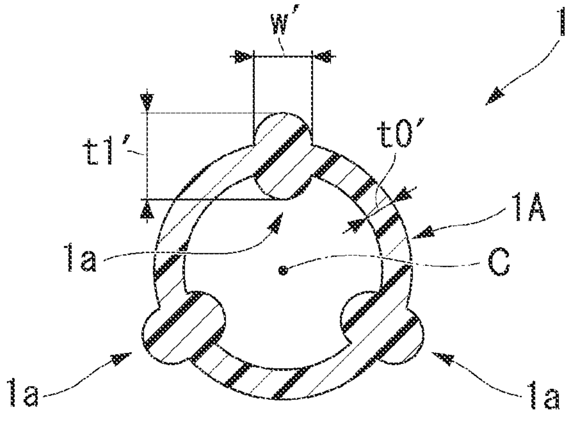
FIG. 6F is a schematic cross-sectional view showing an example of a cross section orthogonal to the central axis of the balloon in the balloon-equipped treatment tool according to the first embodiment of the present invention.

FIGS. 6A, 6B, and 6C show the type of shape of the thick portion 1*a* in the cross section perpendicular to the axis in the first cone portion 1B. In FIGS. 6A, 6B, and 6C, the width of the thick portion 1*a* is represented by w. FIGS. 6D, 6E, and 6F show the type of shape of the thick portion 1*a* in the cross section perpendicular to the axis in the first tail portion 1A. In FIGS. 6D, 6E, and 6F, the width of the thick portion 1*a* is represented by w'.

The types of FIGS. 6A, 6B, and 6C correspond to the types of FIGS. 6D, 6E, and 6F, respectively.

Regarding a width w in the first cone portion 1B and a width w' in the first tail portion 1A of the thick portion 1*a*, as shown in FIG. 5A, when the width of the thick portion 1*a* is narrowed from the proximal end to the distal end, w<w'. As shown in FIG. 5B, when the width of the thick portion 1*a* is narrow at the proximal end and the distal end and wide at the middle, w≈w'. As shown in FIG. 5C, when the width of the thick portion 1*a* is widened from the proximal end to the distal end, w>w'.

A wall thickness t1 in the first cone portion 1B of the thick portion 1*a* and a wall thickness t1' in the first tail portion 1A are determined according to the shape of the thick portion 1*a*.

Regarding a wall thickness t0 of the first cone portion 1B and a wall thickness t0' of the first tail portion 1A other than the thick portion 1*a*, since the first cone portion 1B is stretched and thinned when the balloon 1 is formed, usually t0<t0'.

For example, as schematically shown in FIGS. 6A and 6D, the thick portion 1*a* may be a ridge protruding radially outward from the outer peripheral surface So of the first tail portion 1A and the first cone portion 1B (hereinafter referred to as an outward protruding type). In FIGS. 6A and 6D, the protruding shape of the thick portion 1*a* is drawn in a semicircular shape, but the protruding shape is not limited to this. For example, the protruding shape may be an ellipse, a bell, a triangle, a rectangle, a trapezoid, a polygon, or the like. For example, in each cross-sectional shape, the boundary portion with the outer peripheral surface So may be formed by a smooth curve. Hereinafter, the cross-sectional shapes of FIGS. 6B, 6C, 6E, and 6F are the same.

In the case of the outward protruding type shown in FIGS. 6A and 6D, the shape of the cross section perpendicular to the axis of the inner peripheral surface Si of the first tail portion 1A or the first cone portion 1B is circular. The wall thickness t1 or t1' of the thick portion 1*a* is the distance from the inner peripheral surface Si to the top of the muscle. The wall thickness t1 or t1' may be constant or variable in the extending direction. It is preferable that the wall thickness t1 or t1' of the thick portion 1*a* become monotonously thin in a broad sense from the first tail portion to the first cone portion. In this case, it is suitable because it sufficiently reinforces the vicinity of the boundary between the first tail portion 1A and the first cone portion 1B where stress tends to be concentrated due to bending, and does not hinder the visibility of the narrowed portion of the balloon. The wall thickness t1 or t1' of the thick portion 1*a* is a value obtained by adding the amount of protrusion from the outer peripheral surface So of the muscle to the wall thickness t0 of the first tail portion 1A or the first cone portion 1B or the wall thickness t0' of the first tail portion.

For example, as shown in FIGS. 6B and 6E, the thick portion 1*a* may be a ridge having a width w protruding radially inward from the inner peripheral surface Si (hereinafter referred to as an inward protruding type). In the case of the inwardly protruding type, the shape of the cross section perpendicular to the axis of the outer peripheral surface So is circular. The wall thickness t1 or t1' of the thick portion 1*a* is equal to the distance from the outer peripheral surface So to the top of the muscle. The wall thickness t1 of the thick portion 1*a* is a value obtained by adding the wall thickness t0 of the first cone portion 1B or the wall thickness t0' of the first tail portion 1A to the amount of protrusion from the inner peripheral surface Si of the muscle.

As shown in FIGS. 6C and 6F, the thick portion 1*a* may be a ridge protruding radially outward and inward from the outer peripheral surface So and the inner peripheral surface Si (hereinafter, referred to as an inner/outer protruding type). Here, when the width of the ridges differs between the outer peripheral surface So and the inner peripheral surface Si, the wider width is used to represent the width of the ridges.

The wall thickness t1 of the thick portion 1*a* is equal to the radial distance of the apex of each ridge on the outer peripheral surface So and the inner peripheral surface Si. The wall thickness t1 or t1' of the thick portion 1*a* is a value obtained by adding each protrusion amount from the outer peripheral surface So and the inner peripheral surface Si of the muscle to the wall thickness t0 of the first cone portion 1B or the wall thickness t1' of the first tail portion 1A. In the case of the inner/outer protrusion type, the amount of protrusion of each muscle on the outer peripheral surface So and the inner peripheral surface Si may be the same or different from each other.

FIGS. 6A, 6B, 6C, 6D, 6E, and 6F show an example in which the cross-sectional shapes of the thick portions 1*a* are similar to each other. However, the cross-sectional types of the thick portions 1*a* may be different from each other. For example, in the cross section perpendicular to the axis, two or more of the inward projecting type, the outward projecting type, and the inward/outward projecting type may be mixed as the type of cross-sectional shape of the plurality of thick portions 1*a*.

The type of cross-sectional shape of each thick portion 1*a* may be constant in the axial direction or may differ depending on the position of the cross-sectional section perpendicular to the axis.

For example, the wall thickness t0' of the first tail portion 1A may be 180 μm or more and 250 μm or less. The wall thickness t0' of the first tail portion 1A is more preferably 180 μm or more and 210 μm or less. Within the above wall thickness range, the balloon 1 can be securely fixed to the sheath 2, and the diameter of the balloon 1 when folded is sufficiently small so that it does not interfere with the insertion of the endoscopic treatment tool insertion channel.

For example, the wall thickness t0 of the first cone portion 1B may be 35 μm or more and 120 μm or less. The wall thickness t0 of the first cone portion 1B is more preferably 40 μm or more and 60 μm or less. Within the above wall thickness range, sufficient translucency can be ensured for observing the narrowed portion through the balloon 1 using the objective lens at the distal end of the endoscope while sufficiently maintaining the wall strength of the first cone portion 1B.

As will be described later, the thick portion 1*a* is provided for the purpose of suppressing bump-shaped ridges caused by wrinkles generated in the first tail portion 1A and the first cone portion 1B in the expanded state of the balloon 1. Therefore, it is preferable that the thick portion 1*a* have a wall thickness and a width that can remain at least in the expanded state, rather than being stretched and disappearing by the expansion of the balloon 1. Even when the balloon 1 is expanded at various expansion rates, it is more preferable that the wall thickness and width of the thick portion 1*a* remain at all expansion rates.

For example, from the viewpoint that the effect of suppressing the occurrence of bump-shaped ridges is sufficient, and the diameter of balloon 1 does not increase when folded, the wall thickness t1 or t1' of the thick portion 1*a* may be 180 μm or more and 250 μm or less. The wall thickness t1 or t1' of the thick portion 1*a* is more preferably 180 μm or more and 200 μm or less.

From the same viewpoint, the width w or w' of the thick portion 1*a* may be 1.0 mm or more and 2.0 mm or less. The width w or w' of the thick portion 1*a* is more preferably 1.0 mm or more and 1.6 mm or less.

The balloon 1 may be manufactured, for example, by blow molding using a molding mold that transfers the shape of the expanded state.

For example, a parison tube made of the same material as the balloon 1 is manufactured. As the parison tube, for example, a cylindrical tube is used.

Blow molding is performed by arranging this parison tube inside the above-mentioned molding mold. That is, the parison tube expands toward the inner surface of the molding die, adheres to the molding surface of the molding die, and hardens, so that the shape of the molding surface is transferred to the outer surface of the expanded parison tube. Thereby, the balloon 1 is manufactured.

At that time, the thick portion 1*a* is formed by appropriately setting the shape of the molding die or the molding conditions for blow molding. In order to form the outwardly protruding thick portion 1*a* as shown in FIGS. 6A and 6D, for example, a groove portion for transferring the protruding shape of the thick portion 1*a* may be formed in the molding die. In order to form the inwardly protruding thick portion 1*a* as shown in FIGS. 6B and 6E, for example, the molding conditions are adjusted so that wall thickness unevenness in the circumferential direction occurs when the parison tube is expanded. Similarly, the forming conditions may be adjusted to form the outwardly projecting thick portion 1*a*. In this case, the thick portion 1*a* protrudes inward at the time of molding, but when the fluid F flows into the balloon 1 after demolding, the thick portion 1*a* protrudes outward due to the pressure of the fluid F.

In order to form the inner/outer protruding type thick portion 1*a* as shown in FIGS. 6C and 6F, the manufacturing methods of the outward protruding type and the inward protruding type thick portion 1*a* may be combined.

After that, the assembly of the distal end convex portion 4, the reinforcing wire 3, and the sheath 2 is inserted into the central portion of the balloon 1. The first tail portion 1A and the second tail portion 1E, respectively, are fixed on the outer peripheral surfaces of the distal end portion and the distal end convex portion 4 of the sheath 2.

As shown in (b), (c), and (d) in FIG. 2, the balloon 1 fixed to the distal end convex portion 4 and the sheath 2 is folded so as to have creases such as a mountain fold portion f1 and a valley fold portion f2 by a well-known folding process or the like, and is wound around the reinforcing wire 3 in the balloon 1. In this way, the balloon-equipped treatment tool 10 is manufactured.

In the balloon 1, the first tail portion 1A and the second tail portion 1E are fixed in close contact with the outer peripheral surfaces of the distal end portion and the distal end convex portion 4 of the sheath 2, respectively. Inside the balloon 1, an internal space I through which the fluid F can enter and exit is formed between the proximal end 2*a* and the distal end convex portion 4 through the distal end opening 2*d*.

The balloon 1 is expanded when the fluid F flows into the internal space I. When the pressure of the fluid F increases, the balloon 1 expands, so that an expanded state corresponding to the pressure received by the balloon 1 can be obtained.

Next, the action of the balloon-equipped treatment tool 10 will be described focusing on the action of the thick portion 1*a*.

First, the balloon 1 at the distal end of the balloon-equipped treatment tool 10 is inserted into the narrowed portion of the patient in a reduced state by a well-known procedure using an endoscope. Specifically, the balloon-equipped treatment tool 10 is inserted into the treatment tool channel of the endoscope with the balloon 1 as the distal end. The distal end of the endoscope is located near the narrowed portion. The surgeon looks at the image in front of the distal end of the endoscope and adjusts the position and posture of the distal end of the endoscope so that the opening of the treatment tool channel faces the narrowed portion. After this, the operator inserts the balloon 1 into the narrowed portion by feeding out the balloon-equipped treatment tool 10 from the opening of the treatment tool channel. At this time, the feeding direction of the balloon 1 is a direction parallel to the central axis of the channel for the treatment tool, and the central axis O of the balloon 1 and the central axis C of the sheath 2 are coaxial.

After that, the operator operates the fluid-introducing device connected to the base 5 of the balloon-equipped treatment tool 10 to introduce the fluid F to the inside of the balloon 1 through the sheath 2. As a result, the balloon 1 inserted into the narrowed portion is expanded. The expansion rate of the balloon 1 is selected by the operator according to the narrowed portion.

Figure 7:
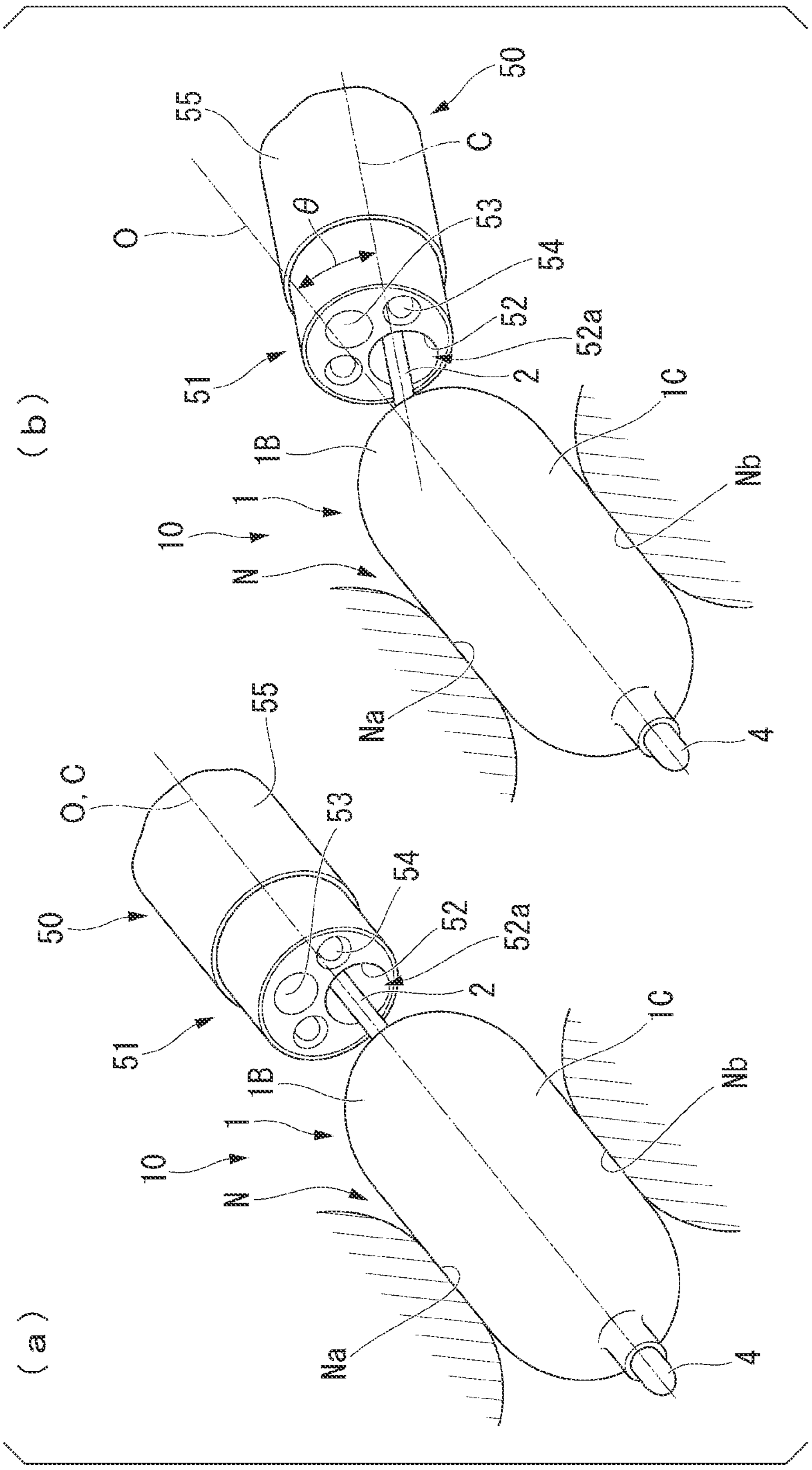
FIG. 7 is an operation explanatory view of the balloon-equipped treatment tool according to the first embodiment of the present invention.

FIG. 7 is an operation explanatory view of the balloon-equipped treatment tool for an endoscope according to the first embodiment of the present invention. For example, FIG. 7A schematically shows how the narrowed portion N is expanded by the balloon 1. The facing distances of the narrowed surfaces Na and Nb facing each other on the inner surface of the narrowed portion N are expanded to a distance equal to the outer diameter of the expanded body portion 1C as compared with before the balloon 1 was expanded.

In the endoscope 50 used for inserting the balloon-equipped treatment tool 10, the distal end portion 51 is fixed to the distal end of the curved portion 55. The operator can change the bending amount and bending direction of the bending portion 55 by operating the operation portion (not shown) of the endoscope 50. As a result, the operator can perform an angle operation for changing the direction of the distal end portion 51 provided at the distal end of the curved portion 55.

An opening 52*a* of the treatment tool channel 52 is opened at the distal end of the distal end portion 51. Further, an imaging unit 53 and an illumination unit 54 are arranged at the distal end of the distal end portion 51.

The imaging unit 53 includes an imaging lens that captures an image in front of the distal end portion 51, an imaging element that photoelectrically converts an optical image formed by the imaging lens, and the like. The image signal photoelectrically converted by the imaging element is transmitted to the proximal end side of the endoscope 50, and an image corresponding to the image signal is displayed on a monitor (not shown).

The illumination unit 54 emits illumination light that illuminates the visual field range of the imaging unit 53.

The optical axes of the imaging unit 53 and the illumination unit 54 and the central axis of the treatment tool channel 52 are all parallel to the central axis of the distal end portion 51.

For example, as shown in FIG. 7A, in a state where the balloon 1 is expanded immediately after the balloon 1 is inserted into the narrowed portion N, the distal end portion 51 faces the entrance of the narrowed portion N. In this case, since the optical axes of the imaging unit 53 and the illumination unit 54 are substantially parallel to the central axis O of the balloon 1, the imaging range of the imaging unit 53 is substantially centered on the center axis O. In order to take a precise image with a high-resolution image, when the narrowed portion is directly imaged without using the light transmitted through the balloon 1, the contact portion between the balloon 1 and the narrowed surfaces Na and Nb does not fall within the imaging range, or even if it does, it is a peripheral portion of the imaging range. Therefore, even if the operator looks at the image on the monitor, the operator may not be able to see whether or not the narrowed portion N is properly expanded, or it may be difficult to see. Further, even when observing the narrowed portion with the light transmitted through the balloon 1, if the sheath 2 or the like greatly enters the observation range, it becomes an obstacle.

The surgeon moves the imaging range for the purpose of making it easier to see the expanded state of the narrowed portion N. Specifically, the surgeon changes the direction of each optical axis of the imaging unit 53 and the illumination unit 54 by performing an angle operation while looking at the image on the monitor.

For example, (b) in FIG. 7 shows a state in which the distal end portion 51 is tilted for the purpose of observing the expanded state in the narrowed surface Na. Since the balloon 1 is restrained by the narrowed portion N, the posture of the balloon 1 does not change as a whole.

Therefore, the central axis of the distal end portion 51 is inclined with respect to the central axis O. Since the treatment tool channel 52 is also inclined with respect to the central axis O, the sheath 2 in the treatment tool channel 52 is inclined with respect to the central axis O like the treatment tool channel 52.

As a result, the balloon 1 is bent in the region of the first tail portion 1A and the first cone portion 1B, which are softer than the sheath 2. For example, the central axis C of the sheath 2 is inclined by θ with respect to the central axis O.

For the purpose of observing the expanded state of the narrowed surface Nb, for example, the operator may incline the distal end portion 51 in the direction opposite to that in (b) in FIG. 7. In this case, although not particularly shown, for example, the central axis C of the sheath 2 may be inclined by about θ in the direction opposite to the central axis O.

As described above, in the procedure for expanding the narrowed portion N by the balloon 1, the first tail portion 1A and the first cone portion 1B are bent in various directions for the purpose of observing the expanded state of the narrowed portion N by the balloon 1.

As the material of the balloon 1, a material having a large shore hardness is often selected for the purpose of achieving high withstand voltage. A material having a large shore hardness has high durability during expansion, but for example, deformation marks such as wrinkles are likely to remain during bending. This tendency is particularly remarkable when the shore hardness is D40 or more. Therefore, even if the balloon 1 is formed of a material having a large shore hardness, there is a strong demand for a technique in which deformation marks are less likely to remain.

Figure 8:
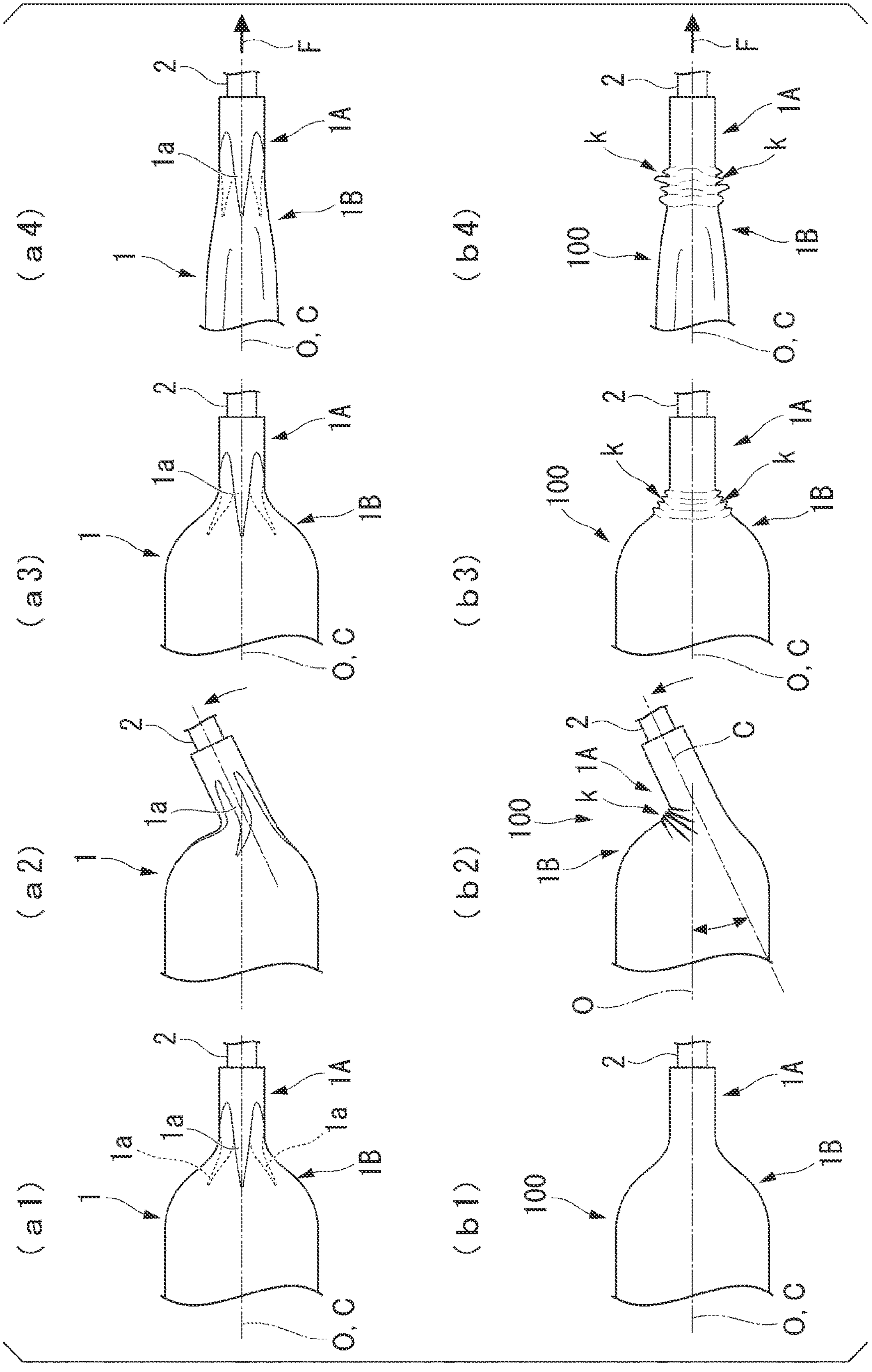
FIG. 8 is a schematic diagram illustrating the operation of a balloon-equipped treatment tool and a comparative example according to the first embodiment of the present invention.

FIG. 8 is a schematic diagram illustrating the operation of the balloon-equipped treatment tool for an endoscope and the comparative example according to the first embodiment of the present invention. In FIG. 8, (b1), (b2), (b3), and (b4) show an example of a balloon 100 as a comparative example.

The balloon 100 of the comparative example has the same configuration as the balloon 1 except that it does not have the thick portion 1*a*. The balloon 100 is fixed to the distal end convex portion 4 (not shown) and the sheath 2 in the same manner as the balloon 1.

When the angle operation of the endoscope 50 (not shown) is performed from the state where the central axes O and C are coaxial (see (b1) in FIG. 8), the first tail portion 1A or the first cone portion 1B in the vicinity of the first tail portion 1A is bent (see (b2) in FIG. 8). At this time, wrinkles k are generated on the balloon 100 inside the bending at the bending portion. If the material is plastically deformed when wrinkles are generated, traces of wrinkles remain. Therefore, even if the central axes O and C are returned to the coaxial state, the wrinkles k remain as deformation marks to some extent.

When the operator observes the expanded state of the narrowed portion N over the entire circumference, it is necessary to operate the angle in various directions. When the angle operation is performed in the other direction, wrinkles k are generated inside the bending of the new bending portion. The new wrinkle k may intersect the existing wrinkle k that has already been formed. In this case, the existing wrinkles k are bent to form more complicated wrinkles, so that the balloon 100 is hardened.

When the angle operation in the same direction or substantially the same direction is repeated, the same wrinkle k is repeatedly formed, which causes a crease, and the wrinkle k may gradually increase.

When the operator finishes observing the dilated state of the narrowed portion N, as shown in (b3) in FIG. 8, a large number of wrinkles k are formed on the distal end side of the first tail portion 1A and the proximal end side of the first cone portion 1B. The wrinkles k are raised like bumps on the outside of the balloon 100.

The balloon 100 is reduced by discharging the fluid F when the expansion of the narrowed portion N is completed (see (b4) in FIG. 8). At this time, if the wrinkles k raised in a bump shape are formed, the outer diameter of the balloon 100 in the reduced state becomes larger than the outer diameter of the first tail portion 1A. If the amount of wrinkle k ridge is too large, it may be difficult for the reduced balloon 100 to be pulled out through the treatment tool channel 52.

On the other hand, in FIG. 8, (a1), (a2), (a3), and (a4) show an example of the balloon 1 of the present embodiment.

According to the balloon 1 of the present embodiment, a ridge-shaped thick portion 1*a* is formed extending on the first tail portion 1A and the first cone portion 1B (see (a1) in FIG. 8).

Since the thick portion 1*a* is thicker than the first tail portion 1A and the first cone portion 1B, it is unlikely to be plastically deformed even if it is bent. Further, since the thick portion 1*a* is ridge-shaped, elastic bending deformation is easier than in the case where the first tail portion 1A or the first cone portion 1B is uniformly thickened.

As a result, as shown in (a2) in FIG. 8, it is possible to suppress the occurrence of wrinkles that form bump-shaped ridges without impairing the flexibility of the balloon 1 in the angle operation.

Therefore, as shown in FIG. 8A4, the outer diameter of the balloon 1 in the reduced state does not become significantly larger than the outer diameter of the first tail portion 1A. As a result, the balloon 1 in the reduced state can be easily pulled out through the treatment tool channel 52.

When the balloon 1 is made of a translucent material and the operator observes the narrowed surface Na in contact with the balloon 1 through the balloon 1, the thick portion 1*a* also has translucency, but the image that has passed through the thick portion 1*a* may be distorted. In order to facilitate observation through the balloon 1, it is more preferable that the thick portions 1*a* adjacent to each other in the circumferential direction have a wide distance. Therefore, as long as there is no problem in suppressing the generation of bumps, it is more preferable that the width of the thick portion 1*a* be narrow as long as the number of the thick portions 1*a* is the same. If the widths of the thick portions 1*a* are the same, it is more preferable that the number of the thick portions 1*a* be small.

Since the balloon 1 abuts on the narrowed portion N at the body portion 1C, in order to make it easier to observe the contact state with the narrowed portion N, it is more preferable that the thick portion 1*a* not extend to the first cone portion 1B near the body portion 1C. For example, if the distal end of the thick portion 1*a* extends to the center of the first cone portion 1B in the axial direction and its vicinity thereof, it is more preferable in that observation through the first cone portion 1B closer to the body portion 1C becomes easier.

When the thick portion 1*a* extends radially from the center of the first cone portion 1B, since the distance between the thick portions 1*a* adjacent to each other in the circumferential direction becomes wider toward the distal end side, it becomes easier to observe the contact state with the narrowed portion N. Similarly, even when the width of the thick portion 1*a* is narrower in the first cone portion 1B than in the first tail portion 1A, since the distance between the thick portions 1*a* adjacent to each other in the circumferential direction becomes wider toward the distal end side, it becomes easier to observe the contact state with the narrowed portion N.

As described above, according to the balloon-equipped treatment tool 10 of the present embodiment, it is possible to suppress the occurrence of bump-shaped ridges in the balloon 1.

First to Fourth Modified Examples

Next, the balloon-equipped treatment tool for an endoscope of the modified example (first to fourth modified examples) of the first embodiment will be described.

Figure 9:
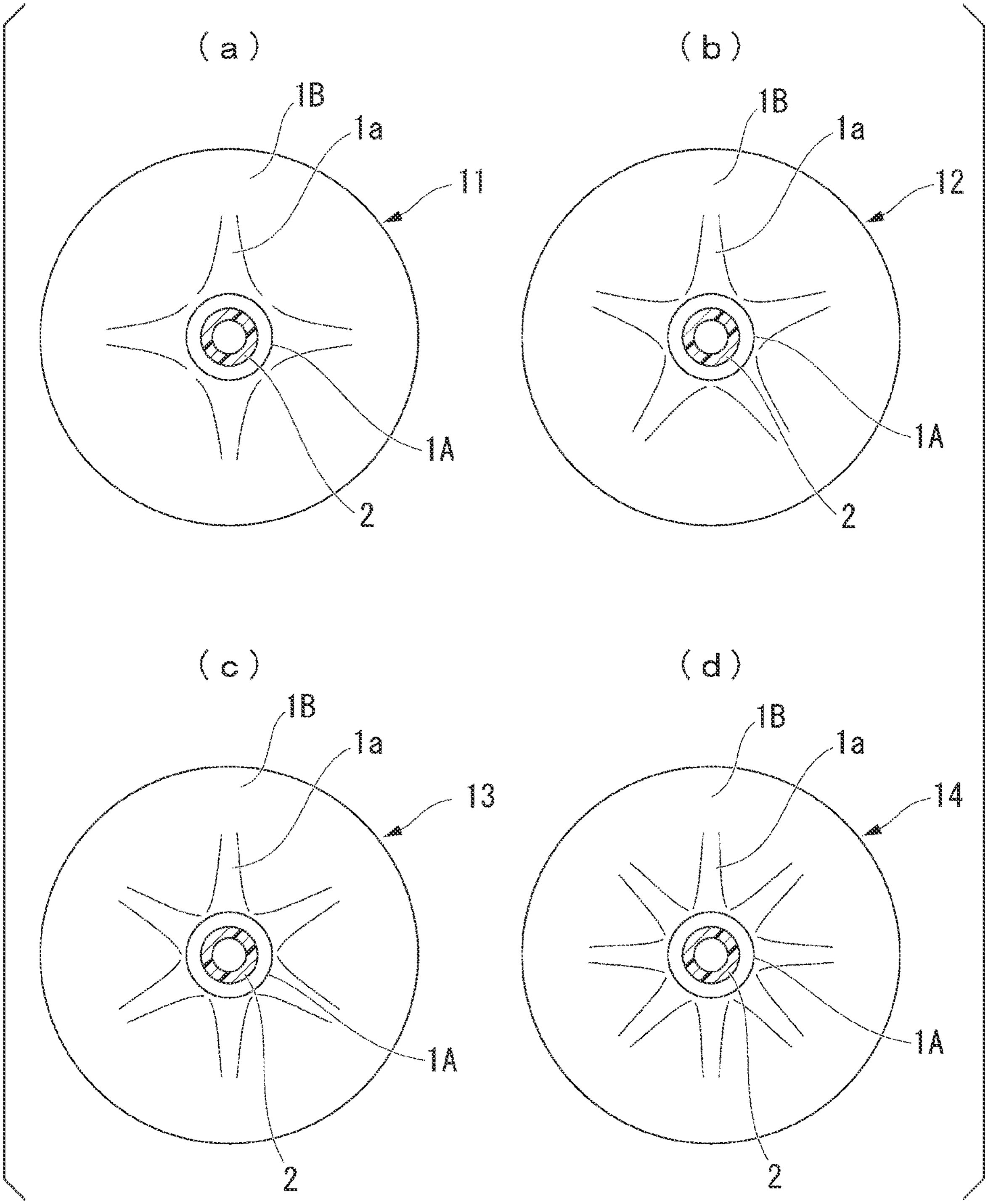
FIG. 9 is a schematic side view showing a balloon in a balloon-equipped treatment tool according to a modification (first to fourth modification) of the first embodiment of the present invention.

FIG. 9 is a schematic side view showing the balloon in the balloon-equipped treatment tool for an endoscope according to the first embodiment of the present invention (first to fourth modified examples).

As shown in FIG. 1, the balloon-equipped treatment tool 10A (balloon-equipped treatment tool for an endoscope) of the first modification includes a balloon 11 instead of the balloon 1 in the first embodiment. Hereinafter, the features different from the first embodiment will be mainly described.

As shown in (a) in FIG. 9, the balloon 11 of this modification is different from the balloon 1 in that it has four thick portions 1*a* similar to those of the first embodiment. Each thick portion 1*a* in the balloon 11 extends radially from the center of the first cone portion 1B. In the example shown in (a) in FIG. 9, each thick portion 1*a* extends in the radial direction that divides the circumference concentric with the first cone portion 1B into four equal parts. The direction in which each thick portion 1*a* viewed from the axial direction extends may be radial without evenly dividing the circumference.

As shown in FIG. 1, the balloon-equipped treatment tools 10B, 10C, and 10D (balloon-equipped treatment tools for endoscopy) of the second modification, the third modification, and the fourth modification include balloons 12, 13, 14 instead of the balloon 1 in the first embodiment. Hereinafter, the features different from the first embodiment will be mainly described.

As shown in (b), (c) and (d) in FIG. 9, the balloons 12, 13, and 14 are different from the balloon 1 in that they have the same thick portions 1*a* as those in the first embodiment, the number of which is 5, 6, and 8, respectively. Each thick portion 1*a* in the balloons 12, 13 and 14 extends radially from the center of the first cone portion 1B. In the example shown in (b), (c) and (d) in FIG. 9, each thick portion 1*a* extends in the radial direction in which the circumference concentric with the first cone portion 1B is divided into five equal parts, six equal parts, and eight equal parts. However, the direction in which each thick portion 1*a* viewed from the axial direction extends may be radial without evenly dividing the circumference.

The balloon-equipped treatment tools 10A, 10B, 10C, and 10D of the first to fourth modifications are configured in the same way as the balloon-equipped treatment tools 10 of the first embodiment, except that the number of thick portions 1*a* in the balloons 11, 12, 13, and 14 is different. Therefore, the balloon-equipped treatment tools 10A, 10B, 10C, and 10D can suppress the occurrence of bump-shaped ridges in the balloons 11, 12, 13, and 14, similar to the balloon-equipped treatment tool 10.

Fifth Modification

Next, the balloon-equipped treatment tool for an endoscope of the fifth modification of the first embodiment will be described.

As shown in FIG. 1, the balloon-equipped treatment tool 10F (balloon-equipped treatment tool for an endoscope) of this modified example includes a balloon 16 instead of the balloon 1 of the first embodiment. Hereinafter, the features different from the first embodiment will be mainly described.

FIGS. 10A, 10B, 10C, and 10D are schematic perspective views showing a balloon used as a balloon-equipped treatment tool for an endoscope according to a fifth modification of the first embodiment of the present invention.

Figure 10A:
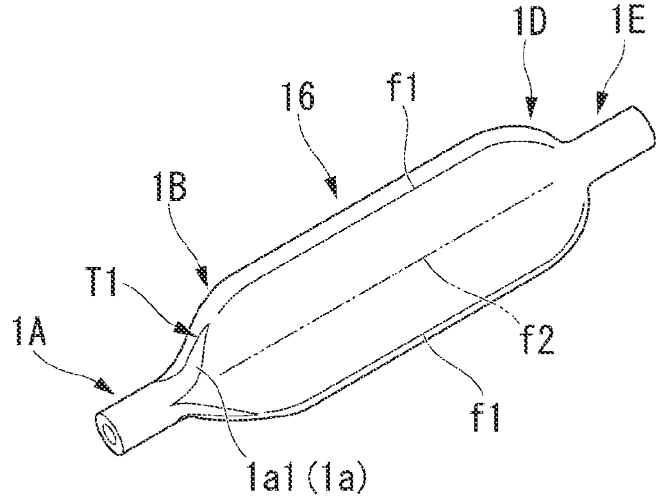
FIG. 10A is a schematic perspective view showing a balloon used as a balloon-equipped treatment tool according to a modified example (fifth modified example) of the first embodiment of the present invention.
Figure 10B:
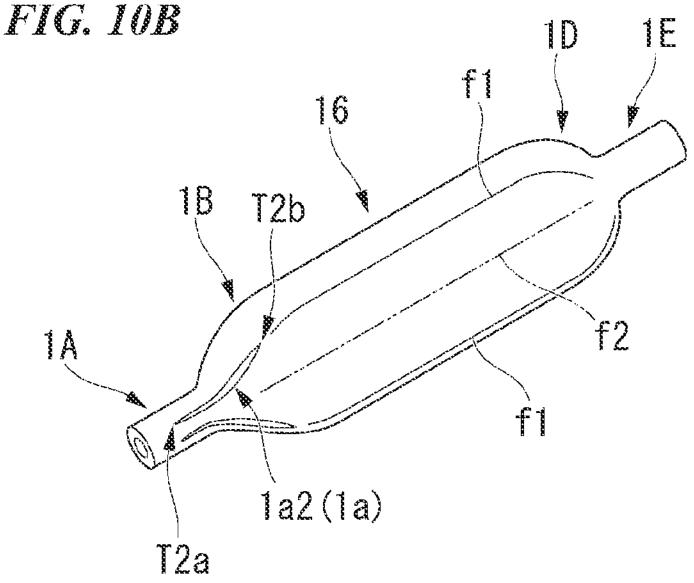
FIG. 10B is a schematic perspective view showing a balloon used as a balloon-equipped treatment tool according to a modified example (fifth modified example) of the first embodiment of the present invention.
Figure 10C:
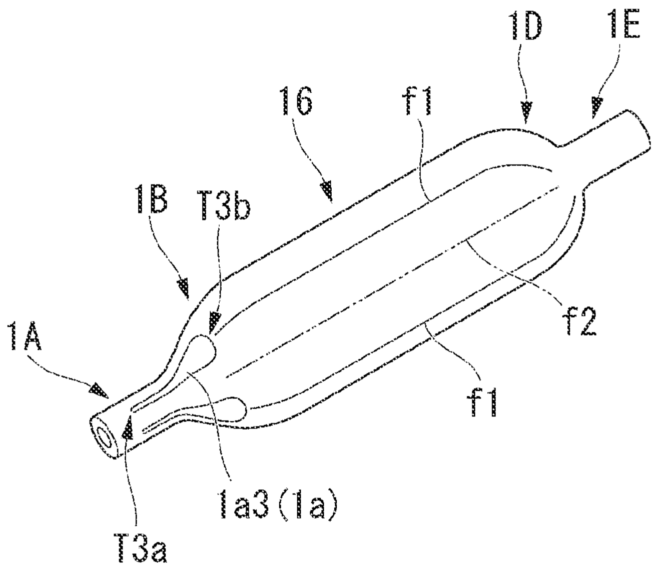
FIG. 10C is a schematic perspective view showing a balloon used as a balloon-equipped treatment tool according to a modified example (fifth modified example) of the first embodiment of the present invention.

In the balloon 16, the thick portion 1*a* is arranged so as to be connected to the mountain fold portion f1 of the balloon fold in relation to the blade BL of the balloon 1 shown in FIG. 2. FIG. 10A corresponds to (a) in FIG. 5, FIG. 10B corresponds to (b) in FIG. 5, and FIG. 10C corresponds to (c) in FIG. 5. In each balloon 16, the mountain fold line f1 at the time of folding the balloon 16 is located on the extension of each of the ridge-shaped thick portions 1*a*1, 1*a*2, 1*a*3. That is, the virtual line in which the ridges of the thick portions 1*a*1, 1*a*2, 1*a*3 are extended along the surface of the balloon 16 overlaps with the mountain fold line f1. With this configuration, when the balloon 16 is folded, the ridges of the thick portions 1*a*1, 1*a*2, 1*a*3 are aligned with the mountain fold line f1 of the blade BL (not shown), so the presence of the thick portions 1*a*1, 1*a*2, 1*a*3 does not interfere with the folding of the blade BL. As a result, the blade BL can be neatly folded and the diameter can be reduced.

The distal ends T1*b*, T2*b*, and T3*b* of each thick portion 1*a*1, 1*a*2, 1*a*3 may extend to the end of the mountain fold portion f1, respectively.

Figure 10D:
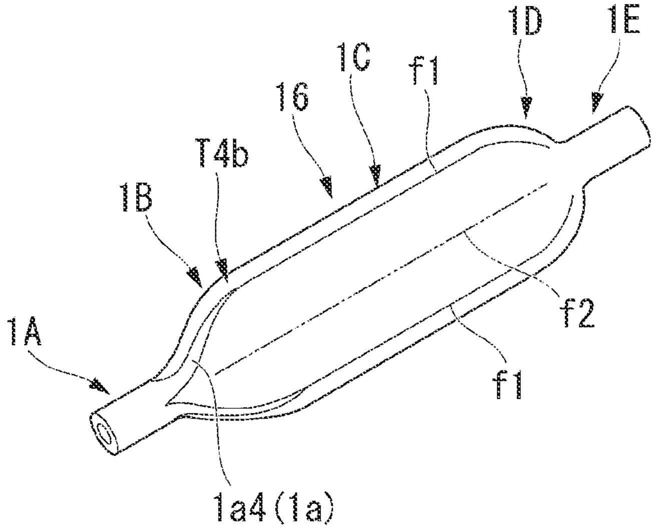
FIG. 10D is a schematic perspective view showing a balloon used as a balloon-equipped treatment tool according to a modified example (fifth modified example) of the first embodiment of the present invention.

For example, as shown in FIG. 10D, the distal end T4*b* of the thick portion 1*a*4 may be located at the body portion 1C which is the cylindrical portion of the balloon 16, and the distal end T4*b* may reach the end of the mountain fold portion f1. In this case, the folding work is guided by each thick portion 1*a*4, which is preferable.

Further, although not particularly shown, even if the thick portion 1*a* is not connected to the folded mountain fold portion f1 and the positions of the two are slightly displaced in the circumferential direction, when the number of thick portions 1*a* extending on the first cone portion 1B and the first tail portion 1A and the number of folding ridges of the body portion 1C are the same, almost the same effect is realized.

Further, even when the number of the thick portions 1*a* extending on the first cone portion 1B and the first tail portion 1A is a multiple of the number of the folded mountain folds f1 of the body portion 1C, or even when the number of folded mountain folds f1 of the body portion 1C is a multiple of the number of the thick portions 1*a* extending on the first cone portion 1B and the first tail portion 1A, almost the same effect is realized.

Sixth Modification

Next, the balloon-equipped treatment tool for an endoscope of the sixth modification of the first embodiment will be described.

Figure 11:
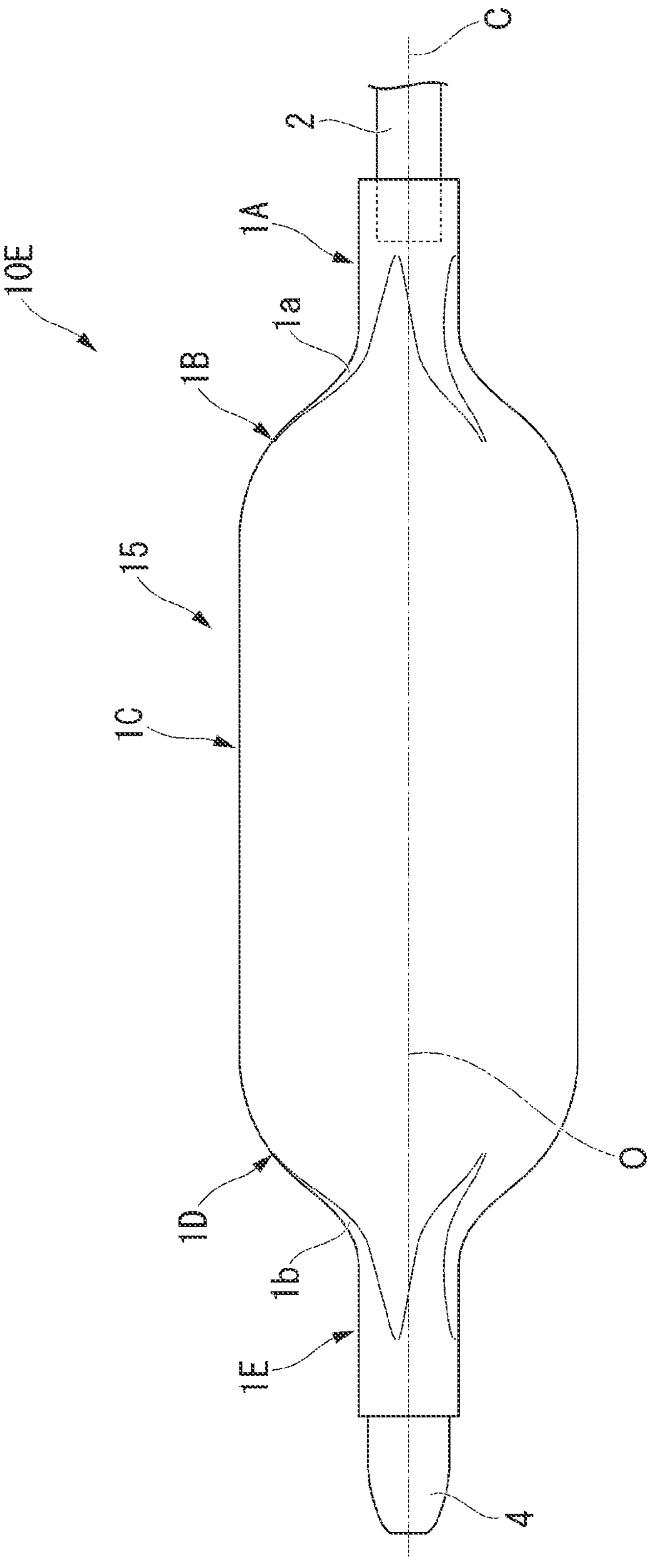
FIG. 11 is a schematic front view showing a balloon-equipped treatment tool according to a modification (sixth modification) of the first embodiment of the present invention.

FIG. 11 is a schematic front view showing a balloon-equipped treatment tool for an endoscope according to a modified example (sixth modified example) of the first embodiment of the present invention.

As shown in FIG. 11, the balloon-equipped treatment tool 10E (balloon-equipped treatment tool for an endoscope) of the fifth modification includes a balloon 15 instead of the balloon 1 in the first embodiment. Hereinafter, the features different from the first embodiment will be mainly described.

The balloon 15 of this modification is different from the balloon 1 in the first embodiment in that a plurality of thick portions 1*b* are formed so as to extend on the second tail portion 1E and the second cone portion 1D.

Each thick portion 1*b* has the same configuration as the thick portion 1*a*. The number of the thick portions 1*b* may be different from the number of the thick portions 1*a*, but in the example shown in FIG. 11, it is the same as the number of the thick portions 1*a*. The position of the thick portion 1*a* in the circumferential direction and the position of the thick portion 1*b* in the circumferential direction may be different from each other, but in the example shown in FIG. 11, the positions in the respective circumferential directions are the same. Therefore, the extension line connecting the distal ends of the thick portions 1*a* and 1*b* facing each other in the axial direction along the surface of the balloon 15 extends in the direction along the central axis O. It is more preferable that the mountain fold portion f1 be formed on this extension line.

Since the balloon 15 has a thick portion 1*b*, it is possible to suppress the occurrence of wrinkles in the second tail portion 1E and the second cone portion 1D. For example, when the distal end convex portion 4 receives an external force and the central axis of the distal end convex portion 4 is inclined with respect to the central axis O of the balloon 15, the balloon 15 is bent near the boundary between the second tail portion 1E and the second cone portion 1D. However, since the thick portion 1*b* has the same structure as the thick portion 1*a*, the occurrence of wrinkles is suppressed at the bent portion as in the case of having the thick portion 1*a*.

In particular, when the thick portion 1*b* has the same configuration as the thick portion 1*a*, the balloon 15 may fix the second tail portion 1E to the distal end of the sheath 2 and the first tail portion 1A to the distal end convex portion 4. In this case, since there is no axial orientation in the manufacture and attachment of the balloon 15, the balloon 15 and the balloon-equipped treatment tool 10E can be manufactured more easily.

Second Embodiment

Next, the balloon-equipped treatment tool for an endoscope of a second embodiment will be described.

Figure 12:
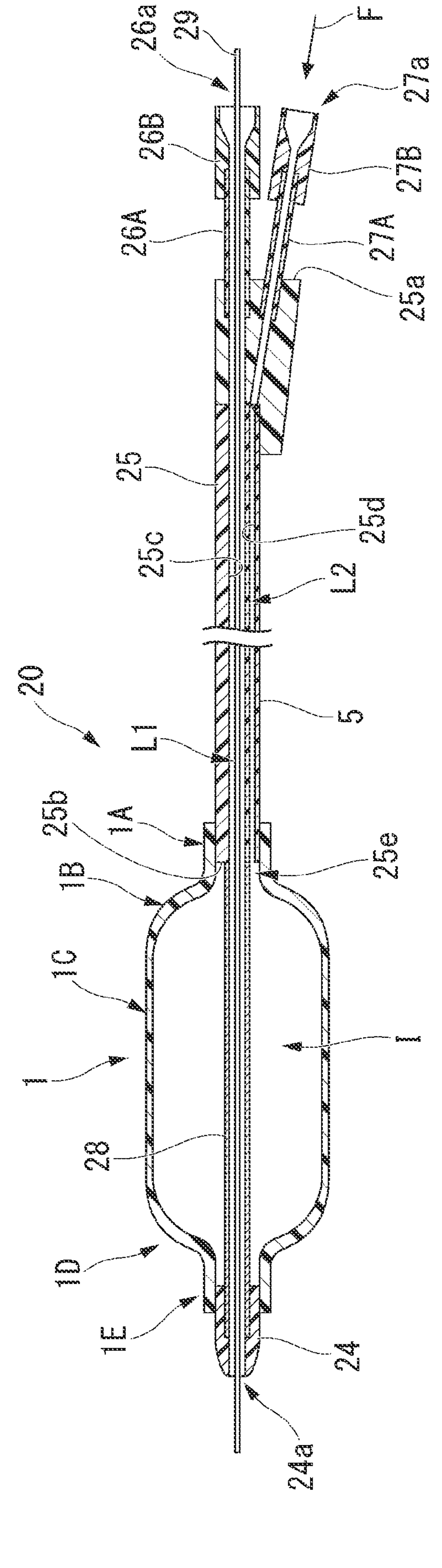
FIG. 12 is a schematic cross-sectional view showing an example of a balloon-equipped treatment tool according to a second embodiment of the present invention.

FIG. 12 is a schematic cross-sectional view showing an example of a balloon-equipped treatment tool for an endoscope according to the second embodiment of the present invention.

The balloon-equipped treatment tool 20 (balloon-equipped treatment tool for an endoscope) of the present embodiment shown in FIG. 12 includes a sheath 25, a shaft 28, and a distal end convex portion 24, instead of the sheath 2, the reinforcing wire 3, and the distal end convex portion 4 in the balloon-equipped treatment tool 10 of the first embodiment. Further, the balloon-equipped treatment tool 20 includes a guide wire lumen tube 26A, a guide wire lumen hub 26B, a fluid-feeding lumen tube 27A, and a fluid-feeding lumen hub 27B instead of the base 5.

Hereinafter, the features different from the first embodiment will be mainly described.

The balloon-equipped treatment tool 20 of the present embodiment is different from the balloon-equipped treatment tool 10 in that it can be inserted into the lumen by using the guide wire 29 placed in the patient's body. For example, as the guide wire 29, a nickel titanium alloy, stainless steel, or the like is used.

The sheath 25 is a long member through which the guide wire 29 is inserted and introduces the fluid F to the internal space I of the balloon 1.

The sheath 25 is composed of a multi-lumen tube having a guide wire lumen 25*c* and a fluid-feeding lumen 25*d* inside. The guide wire lumen 25*c* and the fluid-feeding lumen 25*d* are each independent lumens and penetrate from the proximal end 25*a* to the distal end 25*b* of the sheath 25.

The guide wire lumen 25*c* has an inner diameter through which the guide wire 29 can be inserted.

The fluid F can be distributed in the fluid-feeding lumen 25*d*.

As the material of the sheath 25, the same material as the sheath 2 in the first embodiment may be used.

The shaft 28 is a cylindrical member through which a guide wire 29 extending from the distal end of the guide wire lumen 25*c* is inserted therein. The shaft 28 is also used for the purpose of supporting the balloon 1 substantially coaxially with the sheath 25. However, the shaft 28 has flexibility that allows it to bend depending on the magnitude of the external force acting through the lumen into which the balloon-equipped treatment tool 20 is inserted. Therefore, the shaft 28 can be curved along the lumen.

The inner diameter of the shaft 28 is equal to the inner diameter of the guide wire lumen 25*c*. The shaft 28 is attached to the distal end of the guide wire lumen 25*c* so as to be smoothly connected to the guide wire lumen 25*c*.

The shaft 28 has a length similar to that of the balloon 1 and an outer diameter smaller than the inner diameter of each of the first tail portion 1A and the second tail portion 1E.

The material of the shaft 28 is not particularly limited as long as it is a material that can obtain the same degree of flexibility as the sheath 25. For example, as the material of the shaft 28, nylon, polyamide, PTFE (polytetrafluoroethylene), PE (polyethylene), PP (polypropylene) and the like may be used.

The distal end convex portion 24 is a cylindrical member in which a through-hole 24*a* is formed in the central portion. The inner diameter of the through-hole 24*a* is equal to the inner diameter of the shaft 28. The outer diameter of the distal end convex portion 24 excluding the distal end portion is substantially equal to the inner diameter of the second tail portion 1E. The distal end portion of the distal end convex portion 24 is gradually reduced in diameter and rounded toward the distal end side.

The distal end of the shaft 28 is connected to the base of the distal end protrusion 24 so as to be smoothly connected to the through-hole 24*a*.

The guide wire lumen tube 26A is a cylindrical member through which the guide wire 29 extending from the proximal end of the guide wire lumen 25*c* is inserted into the inside. The inner diameter of the guide wire lumen tube 26A is equal to the inner diameter of the guide wire lumen 25*c*. The guide wire lumen tube 26A is attached to the proximal end portion of the guide wire lumen 25*c* so as to be smoothly connected to the guide wire lumen 25*c*.

At the proximal end of the guide wire lumen tube 26A, a guide wire lumen hub 26B for guiding the guide wire 29 to the lumen of the guide wire lumen tube 26A is provided.

With such a configuration, inside the balloon-equipped treatment tool 20, by providing the guide wire lumen hub 26B, the guide wire lumen tube 26A, the guide wire lumen 25*c*, the shaft 28, and the distal end convex portion 24, a lumen L1 penetrating from the opening 26*a* of the guide wire lumen hub 26B to the through-hole 24*a* is formed. A guide wire 29 can be inserted through the lumen L1.

The fluid-feeding lumen tube 27A is a cylindrical member connected to the proximal end portion of the fluid-feeding lumen 25*d*. The inner diameter of the fluid-feeding lumen tube 27A is substantially equal to the inner diameter of the fluid-feeding lumen 25*d*. The fluid-feeding lumen tube 27A is attached to the proximal end portion of the fluid-feeding lumen 25*d* so as to be smoothly connected to the fluid-feeding lumen 25*d*.

At the proximal end of the fluid-feeding lumen tube 27A, a fluid-feeding lumen hub 27B similar to the base 5 in the first embodiment is provided.

With such a configuration, inside of the balloon-equipped treatment tool 20, by the fluid-feeding lumen hub 27B, the fluid-feeding lumen tube 27A, and the fluid-feeding lumen 25*d*, a lumen L2 is formed that penetrates from the opening 27*a* of the fluid-feeding lumen hub 27B to the opening 25*e* of the fluid-feeding lumen 25*d* that opens at the distal end 25*a*. The fluid F can be distributed in the lumen L2.

In the balloon 1 of the present embodiment, the first tail portion 1A is firmly fixed to the distal end portion of the sheath 25, and the second tail portion 1E is firmly fixed to the proximal end portion of the distal end convex portion 24. As a method for fixing the first tail portion 1A and the second tail portion 1E to the sheath 25 and the distal end convex portion 24, the same fixing method as in the first embodiment can be used.

Inside the balloon 1 in this embodiment, an internal space I communicating with the lumen L2 is formed. Therefore, the fluid F can be introduced to the internal space I through the lumen L2.

The shaft 28 extends along the center of the internal space I in the balloon 1. Both ends of the shaft 28 in the longitudinal direction are connected to the guide wire lumen 25*c* and the through-hole 24*a* without communicating with the internal space I. Therefore, the lumen L1 forms a through-hole that crosses the internal space I without communicating with the internal space I.

The balloon 1 of the balloon-equipped treatment tool 20 of the present embodiment is inserted into the narrowed portion of the patient by a well-known procedure using a guide wire 29 placed in the patient's body and an endoscope. After being inserted into the narrowed portion, the balloon 1 can dilate the narrowed portion in the same manner as in the first embodiment. At that time, the operator can perform an angle operation and perform a procedure for expanding the narrowed portion while observing the expanded state of the balloon 1 in the same manner as in the first embodiment.

Similar to the first embodiment, wrinkles are less likely to occur on the balloon 1 even if the angle operation is performed. Therefore, according to the balloon-equipped treatment tool 20 of the present embodiment, it is possible to suppress the occurrence of bump-shaped ridges in the balloon 1.

In each of the above embodiments and modifications, a case where a thick portion is formed by blow molding a parison made of a cylindrical tube has been described. However, the method for manufacturing the balloon is not limited to this as long as the thick portion can be formed.

As described in the first embodiment, the type of lumen into which the balloon-equipped treatment tool 10 is inserted is not limited. However, in the gastrointestinal tract such as the esophagus, pylorus, bile duct, and large intestine, the angle operation is larger than that of the blood vessel, and the bending load is also large. Therefore, the present invention exerts a more remarkable effect when applied to a balloon-equipped treatment tool for gastrointestinal endoscopy. The same applies to the balloon-equipped treatment tool in each modification and the second embodiment.

Although the preferred embodiments of the present invention have been described above, the present invention is not limited to these embodiments. It is possible to add, omit, replace, and make other changes to the configuration without departing from the spirit of the present invention.

Further, the present invention is not limited by the above description, but only by the claims of the attachment.

According to each of the above embodiments and modifications, it is possible to provide a balloon-equipped treatment tool for an endoscope capable of suppressing the occurrence of bump-shaped ridges in a balloon.

What is claimed is:

1. A treatment tool for use with an endoscope, the treatment tool comprising:
- a balloon; and
- a sheath connected to a proximal end side of the balloon, wherein the balloon comprises:
  - a body portion having a first wall thickness,
  - a tail portion connected to the sheath,
  - a cone portion located between the body portion and the tail portion, and
  - a plurality of ribs having a second wall thickness larger than the first wall thickness,
- the plurality of ribs are formed along the longitudinal direction of the balloon; and
- a width of the plurality of ribs in a circumferential direction is wider in the tail portion than in the cone portion.

2. The treatment tool according to claim 1, wherein a wall thickness of the plurality of ribs in a radial direction is thinner at the cone portion than at the tail portion.

3. The treatment tool according to claim 1, wherein the plurality of ribs are formed radially from a center of the cone portion.

4. The treatment tool according to claim 3, wherein the plurality of ribs are formed at equal intervals in a circumferential direction of the balloon.

5. The treatment tool according to claim 1, wherein a material of the balloon has a shore hardness of D40 or more.

6. The treatment tool according to claim 3, wherein
- the balloon is provided so as to be foldable so that a plurality of blades are formed at different positions in a circumferential direction, and
- the number of the plurality of blades and the number of the plurality of ribs are the same.

7. The treatment tool according to claim 3, wherein
- the balloon is provided so as to be foldable so that a plurality of blades are formed at different positions in a circumferential direction,
- the number of the plurality of blades corresponds to a multiple of the number of the plurality of ribs, or the number of the plurality of ribs corresponds to a multiple of the number of the plurality of blades.

8. A treatment tool for use with an endoscope, the treatment tool comprising:
- a balloon; and
- a sheath connected to a proximal end side of the balloon, wherein the balloon comprises:
  - a body portion having a first wall thickness,
  - a tail portion connected to the sheath,
  - a cone portion located between the body portion and the tail portion, and
  - a plurality of ribs arranged at each of the tail portion and the cone portion,
- wherein a width of at least one rib of the plurality of ribs in a circumferential direction is wider in the tail portion than in the cone portion, and
- the width of the at least one rib varies in the longitudinal direction.

9. The treatment tool according to claim 8, wherein the at least one rib has a distal end arranged in the cone portion and a proximal end arranged in the tail portion.

10. The treatment tool according to claim 8, wherein the at least one rib is formed along a longitudinal direction of the balloon.

11. The treatment tool according to claim 10, wherein
- the balloon is provided so as to be foldable along a plurality of mountain folds and a plurality of valley folds extending in a longitudinal direction thereof, and
- the at least one rib is connected to at least one of the plurality of mountain fold portions in the longitudinal direction.

12. A treatment tool for use with an endoscope, the treatment tool comprising:
- a balloon; and
- a sheath connected to a proximal end side of the balloon, wherein the balloon comprises:
  - a first portion,
  - a second portion connected to the sheath and having a smaller dimension in a radial direction than the first portion,
  - a third portion having an outer surface transitioning between an outer surface of the second portion and an outer surface of the first portion, and
  - a rib having:
    - a circumferential width;
    - a thickness in a radial direction thicker than other portions of one or more of the second and third portions, the thickness decreasing from the second portion to the third portion;
    - a longitudinal length extending at least through a transition point between the second and third portions;
    - the rib is formed along the longitudinal direction of the balloon; and
    - a width of the rib in a circumferential direction is wider in the second portion than in the third portion.

13. The treatment tool according to claim 12, wherein the rib terminates within the third portion.

14. The treatment tool according to claim 1, wherein the plurality of ribs each further having a longitudinal length extending at least through a transition point between the tail portion and the cone portion.

15. The treatment tool according to claim 1, wherein the plurality of ribs each extend continuously in the cone portion and in the tail portion.

16. The treatment tool according to claim 8, wherein a wall thickness of the plurality of ribs in a radial direction is thinner at the cone portion than at the tail portion.

17. The treatment tool according to claim 8, wherein the plurality of ribs are formed radially from a center of the cone portion.

* * * * *